United States Patent [19]
Siegler et al.

[11] Patent Number: 5,824,079
[45] Date of Patent: Oct. 20, 1998

[54] SWELLING TYPE COPOLYMERIC COMPOSITE MATERIAL WITH SELF-FIXATION CHARACTERISTICS

[75] Inventors: Sorin Siegler, Merion, Pa.; Surya Kalidindi, Turnersville, N.J.; Abdel Abusafieh, Philadelphia, Pa.

[73] Assignee: Drexel University, Philadelphia, Pa.

[21] Appl. No.: 702,231

[22] Filed: Aug. 23, 1996

[51] Int. Cl.$^6$ ................................... A61B 17/04
[52] U.S. Cl. ............................. 623/11; 623/16; 524/379
[58] Field of Search ............................ 524/379; 623/11, 623/16, 22, 901

[56] References Cited

U.S. PATENT DOCUMENTS

| | | | |
|---|---|---|---|
| 4,124,748 | 11/1978 | Fujimoto et al. | 526/8 |
| 4,396,476 | 8/1983 | Roemer et al. | 525/193 |

OTHER PUBLICATIONS

Higgins et al., "Soluble High Polymers from Allyl Methacrylate", (1968) *J. Polym. Sci. Part A–1: Polym. Chem.* 6:3007–3012.

Spector et al., A High–Modulus Polymer for Porous Orthopedic Implants: Biomechanical Compatibility of Porous Implants, 1978, *J. Biomed. Mater, Res.* 12:665–677.

Hench et al., *Biomaterials: An Interfafcial Approach,* vol. 4, Academic Press, New York, 1982 (Too voluminous for submission).

El Basty et al., "The Development of a Novel Tooth–Root Implant Material", 1983, *J. Dent. Res.* 62(6):733–737.

Turner et al., "Highly Swollen Hydrogels: Vinyl Pyrrolidone Copolymers", 1986, *Polymer* 27: 1619–1624.

Breznick et al., "Surface Treatment Technique for Aramid Fibers", 1987, *Polymer Communications* 28:55–56.

Morgan et al., "The Characterization of the Chemical Impurities in Kevlar 49 Fibres", 1987, *Polymer* 28:340–346.

Firestone et al., "Dynamic pH–Dependent Swelling Properties of a Hydrophobic Polyelectrolyte Gel", 1988, *Polymer Communications* 29:204–208.

Weber et al., "Hydrophilic–Hydrophobic Two–Component Polymer Networks: 2. Synthesis and Characterization of Poly(Ethylene Oxide)–Linked–Polybutadiene", 1988, *Polymer* 29:1071–1078.

Sharda et al., "A Dynamic Implant for the Development of a Hip Stem Prosthesis", 1990, *Annual International Conference of the IEEE Engineering in Medicine and Biology Society,* 12(5):2182–2183.

El–Sa'ad et al., "Moisture Absorption by Epoxy Resins: the Reverse Thermal Effect", 1990, *J. Mater. Sci.* 25:3577–3582.

Ding et al., "Model Filled Polymers. VI. Determination of the Crosslink Density of Polymeric Beads by Swelling", 1991, *J. Polym. Sci. Part B: Polym. Phys.* 29:1035–1037.

Kabra et al., "Modification of the Dynamic Swelling Behavior of Poly(2–Hydroxyethyl Methacrylate) in Water", 1991, *J. Appl. Polym. Sci.* 42:2409–2414.

Park et al., *Biomaterials: An Introduction,* 2nd Edition, Plenum Press, New York, 1992 (Too voluminous for submission).

King et al., "Development and Evaluation of Surface Treatments to Enhance the Fiber–Matrix Adhesion in PAN–Based Carbon Fiber/Liquid Crystal Polymer Composites. Part 1:", 1993, *Poymer Compsites* 14(4): 292–300.

(List continued on next page.)

*Primary Examiner*—Gary Jackson
*Attorney, Agent, or Firm*—Panitch Schwarze Jacobs & Nadel, P.C.

[57] ABSTRACT

A method of anchoring soft tissue to bone is provided comprising providing a mixture of a hydrophobic monomer and a hydrophilic monomer and a crosslinking agent to form a swellable copolymer, adding a soft tissue attachment element to the mixture, wherein a portion of the soft tissue attachment element protrudes from the mixture, polymerizing the mixture to form the copolymer, implanting the copolymer into bone and attaching a soft tissue to the protruding portion of the attachment element to anchor the soft tissue to the bone.

25 Claims, 27 Drawing Sheets

OTHER PUBLICATIONS

Storey et al., "Bioabsorbable Composites. 1: Fundamental Design Considerations Using Free Radically Crosslinkable Matrices", 1993, *Polym. Compos.* 14(1):7–15.

Wang et al., "Catalytic Grafting: A New Technique for Polymer–Fiber Composites, III. Polyethylene–Plasma–Treated Kevlar™ Fibers Composites: Analysis of the Fiber Surface", 1993, *J. Appl. Polym. Sci.* 48: 121–136.

Ahmed et al., "Towards the Development of a New Class of Swelling Type Hip Implants", 1994, *Thirteenth Southern Biomedical Engineering Conference,* Washington, D.C., pp. 728–731.

Ahmad et al., "States of Water in Poly(Methyl Methacrylate–co–N–Vinyl–2–Pyrrolidone) Hydrogels During Swelling", 1994 *Polymer* 35:9: 1997–2000.

Kowalczuk et al., "Synthesis of New Graft Polymers via Anionic Grafting of β–Butyrolcatone on Poly(Methyl Methacrylate)", 1994, *Macromolecules* 27(2):573–575.

Aoki et al., "Temperature–Responsive Interpenetrating Polymer Networks Constructed with Poly(Acrylic Acid) and Poly(N,N–Dimethylacrylamide)", 1994, *Macromolecules* 27(4):947–952.

Xu et al., "Structural Study of Methyl Methacrylate–α–Trifluoromethacrylic Acid Copolymer by $^1$H–NMR", 1994, *J. Polym. Sci. Part A: Polym. Chemi* 32:2803–2807.

Yoa et al., "Swelling Kinetics and Release Characteristic of Crosslinked Chitosan: Polyether Polymer Network (Semi–IPN) Hydrogels", 1994, *J. Polym. Sci. Part A: Polym. Chem.* 32:1213–1223.

Sharda, "A Self–Anchoring 3–D Braid Reinforced Composite for Orthopedic Implants", 1995, Ph.D. Thesis, Drexel University, Philadelphia, PA, Dec., 1993. pp. 1–90.

Ko et al., "The Influence of Pre–Carbonization on the Properties of PAN–Based Carbon Fibers Developed by Two–Stage Continuous Carbonization and Air Oxidation", 1995, *Polym. Compos.* 16(3):224–231.

Wang et al., "Microstructure/Property Relationships in Three–Dimensionally Braided Fiber Composites", 1995, *Compos. Sci. Technol.* 53:213–222.

Wu et al., "Effects of Treatment on the Surface Composition and Energy of Carbon Fibers", 1995, *Polym. Compos.* 16(4):284–287.

Sclippa et al., "Carbon Fiber Reinforced Polyethylene for Possible Orthopedic Uses", 1973, *J. Biomed. Mater. Res.* 7:59–70.

Greenberg et al., "Stimulation of Bone Formation by a Swelling Endosseous Implant", 1978, *J. Biomed. Mat. Res.* 12:929–933.

Spector et al., "Biomechanical Characterization of Porous Polysulfone Orthopedic Implants," 1978, *Transactions of the 4th Annual Meeting Society for Biomaterials. The 10th Annual International Biomaterials Symposium,* vol. 2:124–125.

Brandrup et al., "Free Radical Copolymerizatino Reactivity Ratios", 1989, *Polymer Handbook (3rd Ediotion)* II–164, Wiley, New York.

Chou et al., "Three–Dimensional Fabrics for Composites", 1989, *Textile Structural Composites,* Elsevier Science Publishers, Amsterdam, vol. 3: pp. 129–157.

Ko, "Preform Fiber Architecture for Ceramic–Matrix Composites", 1989, *Ceramic Bulletin* 66(2):401–414.

Mobarakeh et al., "Improvement of Mechanical Properties of Composites Through Polyamide Grafting Onto Kevlar Fibers" 1996, *Polymer Engineering and Science* 36(6):778–785.

- MMA
- AA
- Cross-linker

SWELLING TYPE COPOLYMERIC COMPOSITE MATERIAL WITH SELF-FIXATION CHARACTERISTICS

FIELD OF INVENTION

The field of the invention is methods and materials for anchoring soft tissue to bone.

BACKGROUND OF INVENTION

Bone implants and anchoring systems in bone have been examined intensively with a view to providing materials which essentially substitute for bone which has become damaged in some manner. For example, swelling type biocompatible structural materials have been proposed as a means of enhancing the fixation characteristics of implants in bone (Greenberg et al. 1978, J. Biomed. Res. 12:922). The concept involved swelling of the implant by absorption of body fluids and achieving fixation at the implant-bone interface by an expansion-fit mechanism. This type of implant was considered as an alternative to both cemented and non-cemented total joint replacements.

The implant of Greenberg et al. (1978, supra) comprises a composite material system based on polyacrylic acid reinforced with nanoscale-alumina particles. Following a series of surgical implantation experiments in canine femurs, these authors established that controlled swelling results in bone deposition along the tissue-implant interface and the exposed cortical surface of the implant specimens, without any adverse tissue response in the form of inflammation or foreign body reaction.

Other implant systems (Sharda et al., 1990, Annual International Conference of the IEEE Engineering in Medicine and Biology Society, 12:2182) include textile composite systems that have superior mechanical properties (in the dry state) when compared to the composite of polyacrylic acid and alumina used by Greenberg et al. (1978, supra). However, both of these systems have two major disadvantages. First, there is a lack of understanding of which specific values of swelling strains and moduli are desirable for the optimal performance of these implants. Second, swelling of the prior art implant materials has been observed to be accompanied by a heavy loss in mechanical properties (moduli and strengths). This degradation could not be controlled and, in fact, the material composite system evaluated by Kamel and Sharda (1990, supra) has good mechanical strength in the dry state but exhibited a near 100% loss in strength upon saturation in free-swelling conditions, rendering it undesirable for use as a swelling type implant.

A comprehensive study of the stress fields and interfacial micromotions in a swelling type total hip arthroplasty has been conducted using finite element techniques (Ahmad et al., 1994, "Toward the Development of a New Class of Cementless Swelling Type Hip Implants", 13th Southern Biomedical Engineering Conference, Washington, D.C.). This study led to the development of a new matrix material, which swells in a controlled manner and at the same time limits the degradation of mechanical properties of the composite to fairly low values. The matrix is a copolymer comprised of a hydrophobic and a hydrophilic polymer.

In addition to bone implants per se and means for fixing bone to bone during healing of fractures and the like, there is a need for the development of materials and methods for anchoring soft tissue to bone. Materials which are suitable for this purpose must be compatible with both the soft tissue and the bone and the surrounding milieu of the region in which the anchor is located. Preferably, such a material should be swellable in order to provide fixation of the material to the bone by an expansion-fit mechanism. Such a swellable material must possess properties which enable it to behave in the same manner as bone in order to avoid bone resorption and stress shielding problems. In other words, the swellable material must comprise a composition which is compatible with bone, with the soft tissue to be anchored, and with the host in general, in order to avoid inflammation in the implant area and even actual rejection of the implant.

There is a long felt need in the art for the development of a suitable swellable material for use in anchoring soft tissue to bone. While several bone anchoring systems have been reported, none of these possesses all of the desirable characteristics for bone anchoring systems as noted herein.

For example, U.S. Pat. No. 5,411,523 discloses a suture anchor and driver combination. A ligament is attached to the bone via the suture. The anchor is formed from a biodegradable polymer material, such as polylactic acid, polyglycolic acid or other polymer ester which is eventually reabsorbed by the body after bone has grown to the ligament. However, this reference does not disclose whether the biodegradable polymer is swellable and does not disclose that swelling of the same is a necessary component of the invention.

Further, U.S. Pat. No. 5,084,050 discloses a bone implant having a hollow body in the shape of a dowel, wherein the dowel may be perforated to allow growth of tissue therein. The dowel may be formed of absorbable or non-absorbable material. The dowel is expandable, being expanded by the insertion of a screw therein, or by being formed of material which is expandable upon contact with bodily fluids. The dowel permits stable locking of screws into bone, and serves as an anchor for fixing sockets, trochanters and for general anchoring of components in artificial joints. This reference does not disclose use of the dowel as an anchor for attachment of soft tissue to bone.

SUMMARY OF THE INVENTION

The invention includes a method of anchoring soft tissue to bone, the method comprising providing a mixture of a hydrophobic monomer and a hydrophilic monomer and a crosslinking agent to form a swellable copolymer; adding a soft tissue attachment element to the mixture, wherein a portion of the soft tissue attachment element protrudes from the mixture; polymerizing the mixture to form the copolymer; implanting the copolymer into bone and attaching a soft tissue to the protruding portion of the soft tissue attachment element to anchor the soft tissue to the bone.

By swellable copolymer is meant a copolymer capable of absorbing fluid and upon absorption of fluid, the volume of the copolymer is increased compared with the volume of the copolymer prior to absorption of fluid.

In one aspect, the hydrophobic monomer is methyl methacrylate and the hydrophilic monomer is acrylic acid.

In one embodiment, the ratio of methyl methacrylate to acrylic acid is from about 60/40 to about 90/10; preferably, the ratio is from about 70/30 to about 80/20 and more preferably, the ratio is 80/20.

In another embodiment, the crosslinking agent is selected from the group consisting of allyl methacrylate (AMA) and diethylene glycol dimethacrylate (DEGDMA) and is preferably AMA.

In another aspect, the mixture further comprises biocompatible fibers. The fibers may be any biocompatible fibers suitable for use in the implant. Preferably, the fibers are carbon fibers or Kevlar fibers and more preferably, the fibers are carbon fibers.

In one embodiment, the fibers are oriented in the copolymer in one direction and in another embodiment, the fibers are in a braided orientation in the copolymer. In yet another embodiment, the fibers comprise chopped fibers.

In yet another aspect, the soft tissue attachment element is inserted into the mixture prior to polymerization of the copolymer, and in another aspect, the soft tissue attachment element is wound around the copolymer after polymerization of the copolymer.

The soft tissue attachment element may be a metal or may be made of a flexible material. The flexible material may be suture-like or may be actual suture material.

The invention further includes a composite for anchoring soft tissue to bone comprising methyl methacrylate and acrylic acid in a ratio of 80/20, allyl methacrylate, braided carbon fibers, a soft tissue attachment element attached to the composite so as to partially project therefrom.

By the term "composite" as used herein, is meant a copolymer of a hydrophobic and a hydrophilic monomer, a crosslinking agent and optionally, biocompatible fibers.

Also included in the invention is a preformed object for anchoring soft tissue to bone. The preformed object comprises a composite material comprising methyl methacrylate and acrylic acid in a ratio of 80/20 and allyl methacrylate. The preformed object may further comprise biocompatible fibers and even a soft tissue attachment element attached to the composite material so as to partially project therefrom.

The preformed object of the invention may be a screw, a pin or a staple or other like structure suitable for insertion into bone and attachment of soft tissue thereto.

DETAILED DESCRIPTION OF PREFERRED EMBODIMENTS

Figure 1:
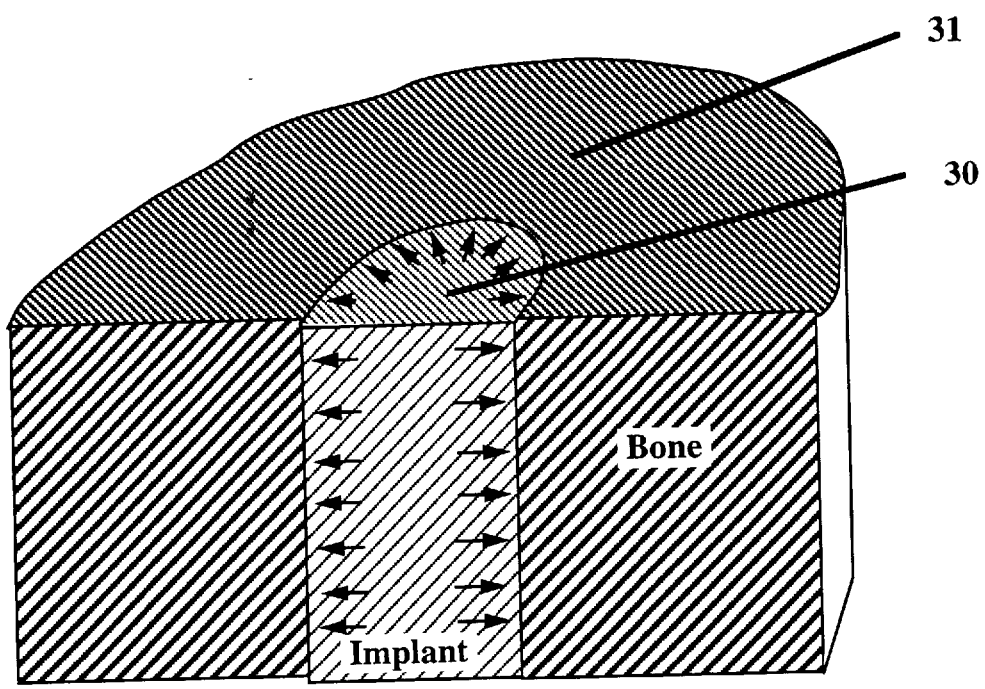
FIG. 1 is a schematic drawing of a longitudinal section of swelling type material 30 implanted in bone 31 demonstrating the expansion-fit mechanism. The arrows indicate the interfacial pressure induced by swelling of the implant.

Orthopedic surgery includes a large number of clinical applications in which good fixation to bone is of primary importance. Examples include fixation of plates or intramedullary rods for fracture fixation, spinal stabilization appliances applied following decompression procedures; fixation of soft tissue such as ligaments and tendons to bone during soft tissue reconstructive surgery, and fixation of total joint replacements, etc.

The most common fixation methods include screws, use of grouting agents such as PMMA, and press-fit of the implant to bone. All of these techniques have some severe limitations. For example, screws tend to loosen after repeated cyclic loading as occurs in the body. They also have a severe limitation when good fixation to trabecular bone or to osteoporotic bone is required. The use of bone cement or press-fit techniques for total joint arthroplasties suffer from problems associated with bone resorption, micromotion, and cement failure.

In contrast to present state-of-the art for bone fixation, the instant invention utilizes an expansion-fit mechanism of the swelling type implant. The advantages of this invention include (a) the ability to pre-stress the bone or improve the bone-implant fixation by controlled swelling of the implant, (b) good structural properties of the composite implant in all directions, especially those related to fracture, fatigue resistance and impact, (c) flexibility in designing and tailoring the mechanical properties of the implant, and (d) possibility of low cost manufacturing complex shaped components.

Specifically, the swelling type implant can offer a clinically viable alternative to both cemented and non-cemented total joint arthroplasties. Swelling type implants can overcome the loosening problems commonly associated with both cemented and cementless traditional implants. The swelling of the implant results in a uniform radial compressive pressure on the entire bone-implant interface which leads to better fixation of the implant. Consequently, the swelling type implants are expected to exhibit significantly lower micromotions (which enhance bone-growth) and lower stress concentrations/shielding effects (which together with the tensile hoop stress introduced in the bone mitigate bone resorption).

Swelling of the implant against the bone provides immediate and rigid fixation without using bone cement, while bone ingrowth into the porous surface of the material provides long-term fixation. Eliminating bone cement removes the possibility of "cement disease" or bone resorption due to the presence of the acrylic bone cement. The ability to tailor the mechanical properties of the implant material minimizes the problems associated with micromotion such as thigh pain, reduced or no bone ingrowth, and loosening.

The swelling type implant can also offer a clinically viable alternative to screw fixation techniques. Pins made of the swelling type material can successfully replace the conventional orthopedic screws which are known to have severe deficiencies particularly related to screw loosening with repetitive cyclic loading and poor fixation properties to trabecular bone and to osteoporotic bone. In contrast, the swelling type pins provide excellent fatigue resistance with minimal loosening with repetitive loading. Also, unlike the conventional screw which has high stress concentration in the region of the threads, the invention provides even uniform pressure distribution. Therefore, it is envisioned that the swelling type pin may successfully replace the conventional screw in applications requiring fixation to trabecular bone, osteoporotic bone, or those requiring improved fatigue resistance, such as in fracture fixation, anchoring for soft tissue for reconstructive surgery, and spinal fixations.

The invention provides the medical community with a new class of swelling type composite material for anchoring soft tissue to bone, that provides better short and long term fixation characteristics when compared with traditional bone fixation techniques. Specifically, the new material provides excellent alternatives to conventional orthopedic bone fixation techniques used in applications such as soft tissue attachment to bone during reconstructive surgeries, better spinal fixation appliances, improved fixation to bone of fracture stabilization plates, improved fixation of total joint arthroplasties, etc.

The swelling-type composite material of the invention has significant advantages over that disclosed in U.S. Pat. No. 5,411,523, since the material of the present invention is not biodegradable and thus remains in the bone for the purpose for which it was inserted therein, namely as an anchor. In contrast, the material disclosed in U.S. Pat. No. 5,411,523 is biodegradable and thus is resorbed in the body with time post implantation. For this reason, the material disclosed in U.S. Pat. No. 5,411,523 cannot be used in the present application.

Thus, a swelling type composite material, capable of self-fixation to bone, has been developed for bioimplant applications. The swelling of this material is the result of absorption of surrounding body fluids insitu after implantation, and this swelling results in an expansion-fit to the bone (FIG. 1). The swelling material comprises a co-polymer which is a mixture of a hydrophobic polymer and a hydrophilic polymer matrix reinforced by fibers. The hydrophobic polymer is preferably MMA and the hydrophilic polymer is preferably AA. The copolymer may have embedded in it biocompatible fibers, preferably graphite fibers, which may be uniaxial, chopped or braided to confer strength to the copolymer in several different directions. By changing the relative ratio of hydrophobic to hydrophilic polymers in the copolymer matrix, the amount of swelling at saturation of the material may be controlled thereby providing a means for controlling the mechanical properties of the material.

The ratio of MMA/AA in the copolymer may be from about 90/10 to about 60/40. Preferably, the ratio is about 70/30 and most preferably, the ratio is about 80/20.

A crosslinking agent is used to form the copolymer of the invention. The crosslinking agent may be any biocompatible crosslinking agent which serves to form a crosslink between the hydrophobic monomer and the hydrophilic monomer and which provides the desirable characteristics of the copolymer as described herein. Preferably, the crosslinking agent is one of either AMA or DEGDMA. Most preferably, the crosslinking agent is AMA. The crosslinking agent is added to the hydrophobic and hydrophilic polymer mixture at a concentration ranging from 1–30%, preferably, 5–20%, and most preferably, the crosslinking agent is present in the mixture at a concentration of about 10% by volume. Regarding the amount of crosslinker to be added, it is important that sufficient crosslinker is added to the mixture to ensure complete polymerization of the components of the copolymer. Thus, the amount of crosslinker to be added may vary depending upon the precise concentration of the components in the copolymer and is normally added at a concentration of about 10 % of the total volume of the mixture.

Biocompatible fibers, preferably either carbon or Kevlar fibers, may be added to the copolymer to provide additional strength and stability. These fibers may be added such that they are oriented in the resulting composite in only one direction, or they may be oriented in a braided fashion as exemplified herein. Alternatively, the fibers may be chopped fibers. Preferably, the fibers are carbon (graphite) fibers and more preferably, the fibers are present in the composite in a three-dimensional braided configuration.

Thus, the variables in the design of the composite include (i) composition of the matrix (ratio of MMA/AA), (ii) degrees and types of crosslinking in the matrix, (iii) composition of the biocompatible fibers (graphite, Kevlar, or other fibers), (iv) fiber preform architecture and fiber orientation, and (v) volume fraction of fibers. These variables have a strong impact on the hygro-mechanical properties of the produced composite, and consequently on the performance of the proposed implants.

Desirable hygro-mechanical properties of a swelling composite type material for use in anchoring soft tissue to bone include, but are not limited to the following: controllable swelling strains which accommodate differences in bone structure and properties from person to person depending on age and other factors; a fairly short time to achieve half the saturated swelling strain because this determines how long the patient must remain immobilized; low loss of mechanical properties with swelling; having an elastic stiffness which is close to the elastic stiffness of bone because implants which have a very different elastic stiffness from that of bone (such as currently used metallic implants) cause bone resorption due to stress shielding; and, excellent failure resistant properties.

The process of producing a composite for anchoring soft tissue to bone comprises obtaining a mixture of AA and MMA monomers in the desired ratio to which is added an initiator, usually an initiator which belongs to the family of azobis or peroxide initiators. A suitable crosslinking agent is also added to the mixture. The braided preformed screw, suture or other element is then placed in the mixture such that a portion protrudes therefrom, and the resulting mixture is degassed to eliminate air. This mixture is then placed in a water bath at about 28° C. and the temperature is slowly raised (about 1–2° C./day) until polymerization is complete. The sample is then placed in an oven and heated at about 2 ° C. per minute to about 75° C. and soaked at that temperature for about two hours. The temperature is then further increased to about 130° C. and once again the composite is soaked at that temperature for two hours. The desired shape is cut from the now formed composite structure for insertion into the bone.

Figure 26:
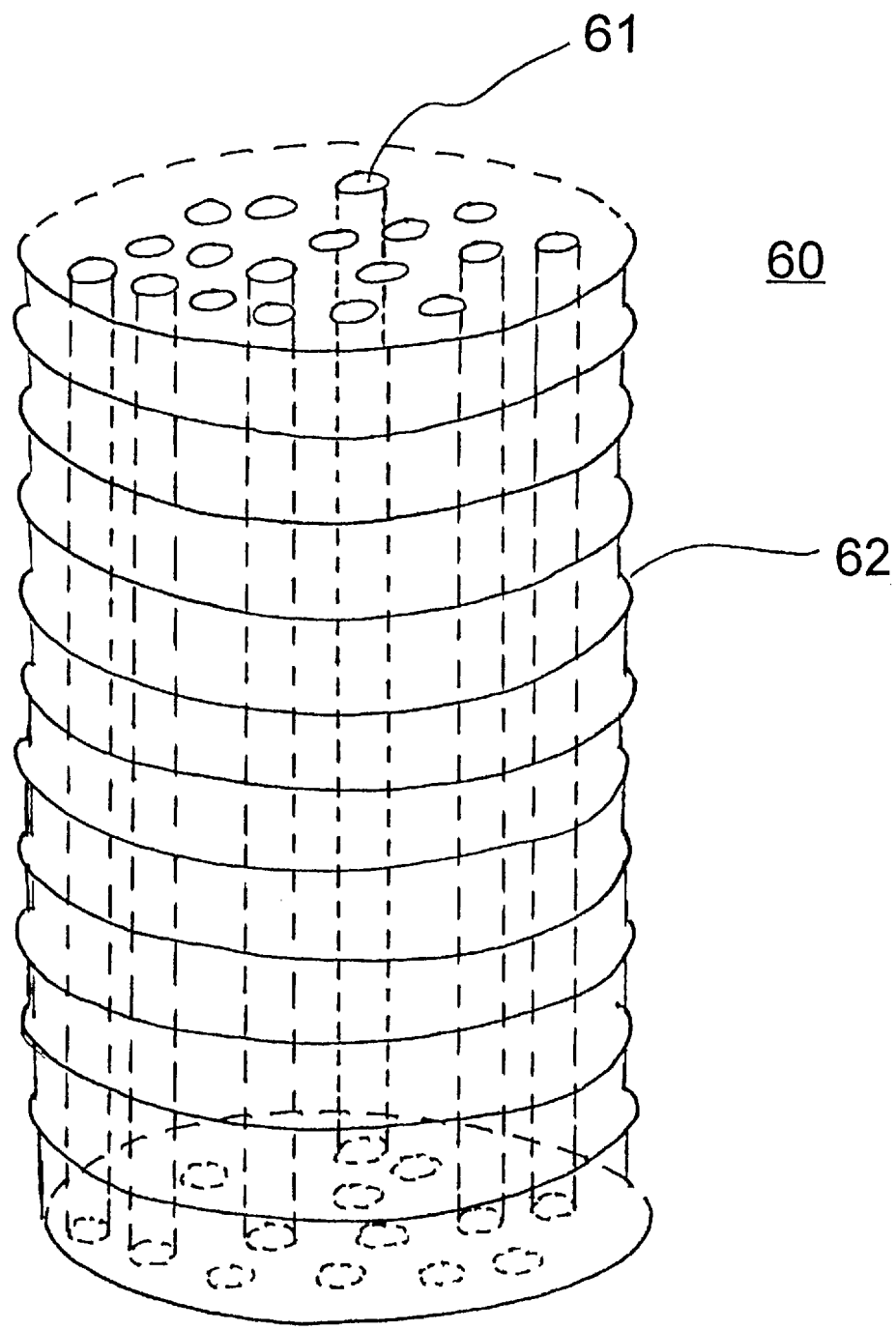
FIG. 26 is a diagram of a screw comprising MMA, AA, AMA and biocompatible fibers.

When the composite is a preformed object such as a screw, pin or staple-type structure, the composite is formed in a mold such that the appropriate shape is achieved upon polymerization of the mixture. When the preformed object also comprises biocompatible fibers, the fibers are preferably present in the center of the structure, i.e., in the backbone of the structure. FIG. 26 is an example of a preformed screw 60 having biocompatible fibers 61 present in the center of the screw and threads 62 present on the outside surface of the screw. The threads 62 may be eliminated thus forming a pin, and when the structure is formed in a mold in the shape of a stable, the preformed structure is a staple.

Attachment of soft tissue to bone may be accomplished in several different ways depending on the type and location of the bone to which the tissue is to be attached and depending on the type of soft tissue to be attached to the bone. The soft tissue is attached to the composite and therefore to the bone by providing in the composite an element which permits attachment of the soft tissue. Thus, prior to formation of the composite, an element for attaching soft tissue is imbedded in or threaded around the composite, such that it is securely positioned therein and having a portion thereof extending from the composite for attachment of the soft tissue. The element for attachment may comprise a screw or a pin type structure which is comprised of a biocompatible material or even a metal if the screw is not in direct contact with the bone. As noted above, the screw or pin structure may even comprise the composite polymer of the invention which is formed prior to formation of the actual plug to be inserted into the bone.

Figure 27:
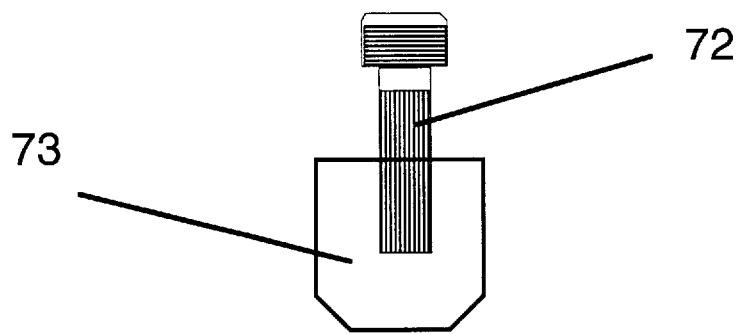
FIG. 27 is a photograph of an embodiment of a composite structures having a soft tissue attachment embedded therein.

The element for attachment may also comprise any biocompatible, flexible material to which soft tissue may be attached. For example, the attachment element may comprise suture like material, or may comprise an actual suture. An examples of a copolymer structures having soft tissue attachment element inserted therein is shown in FIG. 27. The soft tissue attachment element 72 may be a screw as shown, or may be a flexible material embedded in the composite material 73.

Attachment of soft tissue to the bone may be accomplished by first inserting a screw or a flexible material into the unformed composite to which the soft tissue is to be attached after formation of the composite. Alternatively, the attachment element may be wound around the composite, having a portion protruding therefrom, prior to implantation into bone. A hole is drilled in the bone, the composite containing the attachment element is then inserted into the hole and the soft tissue is attached to the attachment element by any appropriate method including stitching, tying and the like. The region containing the implant in the patient is then immobilized until swelling and therefore fixation of the implant is complete. This is estimated to take up to about seven days.

As an alternative embodiment, it should be understood that the copolymer matrix could also be used alone, without the addition of a braided structure, or even unbraided or chopped fibers. In this manner, the matrix has mechanical properties different from those of the braided fiber reinforced structure, that might be suitable in some applications involving soft tissue anchorage or anchorage to osteoporotic/trabecular bone.

As a further embodiment, the copolymer may be provided merely with single sutures, screws or other like soft tissue attachment elements. The copolymer is intended to be used with virtually any mechanical attachment element which may be attached or is considered for attachment directly to bone or which has previously been used to attach soft tissue to bone or other soft tissue, including in addition to sutures and suture-like materials, staples, etc.

It should also be noted that the copolymer matrix can be threaded externally to obtain immediate fixation (like a screw) or internally, in which a screw could be fastened.

The material used in the present invention is a substantive improvement over the original swelling composite system disclosed by Greenberg et al. (1978, supra) which consisted of polyacrylic acid having alumina particles embedded therein and being further reinforced with braided fibers. A major improvement in use of the material of the present invention is the fact that the properties of the copolymer may be tailored to specific orthopedic applications. Thus, while the material disclosed in Greenberg et al. (1978, supra) lost nearly 100% of its mechanical properties when in an aquatic environment, the present material maintains over 85% of its dry state properties when in the saturated state. This permits the use of the composite material of the invention in several different orthopedic implant applications.

Many samples of the proposed swelling type composite material have been constructed as described herein. These samples primarily comprise cylindrical pins of approximately ¼ inches in diameter. A circular braiding pattern of graphite fibers is also described as discussed in Sharda and Kamel (1990 supra), the disclosure of which is hereby incorporated herein by reference.

As described herein, a detailed experimental study was conducted to investigate the swelling and self-fixation characteristics of the composite material. Cylindrical samples of the material were immersed in saline solution for extended periods of time, while weight and volume changes were monitored periodically. These results were used to determine saturation swelling strains and diffusion coefficients for various copolymer compositions. In addition, simple compression tests were performed at various saturation levels to determine the elastic moduli and strength of the composite. Cylindrical samples of the material were implanted into coupons of bovine bone and allowed to swell for various lengths of time. Push-out tests were then conducted in order to determine the self-fixation properties of the implant.

The results of the experiments described herein establish that the swelling strain in the material reaches an asymptotic value at saturation and that this value is strongly influenced by the ratio of hydrophobic to hydrophilic polymers in the copolymer matrix. It was also observed that the percentage of degradation of material properties compared to the dry state was directly related to the amount of swelling. The results of the push-out tests demonstrate excellent fixation to bone and provide guidelines for choosing the proper copolymer composition to achieve optimal fixation with minimal degradation in material properties.

Preliminary push-out tests conducted on samples of this material embedded in porcine femurs and bovine cortical bone showed excellent fixation to bone in comparison with commercially available orthopedic screws and the like. With the material properties achieved and the results obtained, the most suitable type of applications for this material are in the areas of soft tissue fixation to bone, alternatives to the present fixation means in osteoporotic or trabecular bone (cancellous screws, pedicle screws, etc.), and incorporation in total joint replacement.

The general use of the invention is in the areas requiring good fixation to bone such as in orthopedic surgery and dentistry. These include the following:

(1) A system for anchoring soft tissue or artificial grafts to bone. Such a system is needed for reconstructive surgery, for example using an artificial or natural graft for torn ACL at the knee; tendon transfer procedures in the hand, etc. Such systems may include imbedding an appropriate attachment element like a suture material or fabric matrix in the copolymer with one end protruding from the copolymer, so that the tendon or ligament may be attached to the protruding end;

(2) Replacing the bone screws for fracture fixation plates and intramedullary rods with pins made of the swelling type composite;

(3) Replacement of pedicle screws for spinal fixation with pins made of the swelling type composite;

(4) Providing a stable anchoring system for artificial teeth; and (5) Development of non-cemented total joint arthroplasties.

The experiments described below exemplify how to make and use the invention. The invention should not be construed to be limited solely to these examples, but instead should be construed to encompass any and all variations thereof within the broad scope of the invention.

Studies on the Copolymer

Polymer Synthesis

The polymeric is comprised essentially of an MMA backbone with varying amounts of AA monomer which provide affinity of the polymer for water. The introduction of AMA or DEGDMA as crosslinking agents to the copolymer results in the formation of a three-dimensional network. A list of the monomers used in this study, along with some of their chemical and physical properties, is given in Table 1.

TABLE 1

DETAILS OF MONOMERS AND CROSS-LINKING AGENTS USED IN THIS STUDY

| MATERIAL | DENSITY (g/cc) | FORMULA WEIGHT (g/mol) | CONCENTRATION (%) | MOLAR VOLUME (cc/mol) |
|---|---|---|---|---|
| MMA | 0.936 | 100.12 | 99 | 9.255 |
| AA | 1.051 | 72.06 | 99 | 14.439 |
| AMA | 0.938 | 126.16 | 98 | 7.286 |
| DEGDMA | 1.082 | 242.27 | 95 | 7.243 |

All chemicals used in the study were purchased from Aldrich Chemical Co., Milwaukee, Wis., and were used as received without additional purification. Polymerization was carried out in bulk, using a free radical mechanism with 2,2'-azobis 2,4-dimethylvaleronitrile (E. I. Dupont de Nemours & Co., Wilmington, Del.) as the initiator. The initiator was added to varying volumetric ratios of MMA/AA monomers and mixed thoroughly. The desired amount of crosslinking agent (AMA or DEGDMA) was added to the mixture which was stirred manually for ten minutes prior to polymerization. In all cases, the amount of initiator was fixed at 0.4g/100 ml of total mixture.

Polymerization was carried out in a sealed water bath which provided uniform and accurate temperature control. The reaction mixture was poured into glass tubes, sealed with parafilm paper and placed vertically in a glass stand inside the water bath. The assembly was maintained at 30° C. for five hours, then the temperature was raised gradually (5° C. per hour) to 70° C. and was maintained at 70° C. for ten hours followed by overnight cooling. Hereinafter, this heating cycle is referred to as primary curing. The tubes containing the mixture were taken out of the bath and broken under slight clamp pressure.

The samples were then removed from the glass tubes (no noticeable bonding to the tubes occurred) and were placed in an oven where the temperature was raised slowly (1° C. per minute) to 150° C. and the samples were maintained at that temperature for three hours followed by overnight cooling thereby producing the desired crosslinked copolymer. This latter heating cycle is hereinafter referred to as post-curing. The resulting samples were placed in a desiccator containing silica gel crystals to exclude moisture until use.

It was observed that higher heating rates than the those described above usually resulted in the formation of bubble-like domains in the upper parts of the samples during the primary curing cycle and the formation of uniformly distributed thin flakes during post-curing. Both defects disappeared completely when the heating cycles were performed at lower rates.

Characterization of the Polymer

A variety of polymer samples having differing ratios of AA, MMA, and crosslinking agent (AMA or DEGDMA) were synthesized using the procedure described above. All sample compositions used in this study are based on the volumetric ratios of the constituents in the monomer mix and are summarized in Table 2.

TABLE 2

COMPOSITIONS OF SAMPLES USED IN THIS STUDY BASED ON THE RATIOS OF THE DIFFERENT COMPONENTS IN THE MONOMER MIX.

| | % VOL. % | | | % MOL. % | | |
|---|---|---|---|---|---|---|
| SAMPLE | MMA | AA | C.L.A.* | MMA | AA | C.L.A.* |
| PAA[0] | 0 | 100 | 0 | 0 | 100 | 0 |
| 50/50[0] | 50 | 50 | 0 | 39.06 | 60.94 | 0 |
| PMMA[0] | 100 | 0 | 0 | 100 | 0 | 0 |
| 50/50[3A] | 48.54 | 48.54 | 2.91 | 38.35 | 59.84 | 1.81 |
| 60/40[3A] | 58.25 | 38.83 | 2.91 | 49.09 | 50.02 | 1.89 |
| 70/30[3A] | 67.96 | 29.13 | 2.91 | 58.74 | 39.28 | 1.98 |
| 80/20[3A] | 77.67 | 19.42 | 2.91 | 70.44 | 27.48 | 2.08 |
| 90/10[3A] | 87.38 | 9.71 | 2.91 | 83.36 | 14.25 | 2.19 |
| PAA[5A] | 0 | 95.24 | 4.76 | 0 | 97.54 | 2.46 |
| 50/50[5A] | 47.62 | 47.62 | 4.76 | 37.89 | 59.12 | 2.98 |
| 60/40[5A] | 57.14 | 38.10 | 4.76 | 47.49 | 49.40 | 3.11 |
| 70/30[5A] | 66.67 | 28.57 | 4.76 | 57.97 | 38.77 | 3.26 |
| 80/20[5A] | 76.19 | 19.05 | 4.76 | 69.48 | 27.10 | 3.42 |
| 90/10[5A] | 85.71 | 9.52 | 4.76 | 82.16 | 14.24 | 3.59 |
| PMMA[5A] | 95.24 | 0 | 4.76 | 96.21 | 0 | 3.79 |
| 50/50[7.5A] | 46.51 | 46.51 | 6.98 | 37.34 | 58.25 | 4.41 |
| 50/50[10A] | 45.45 | 45.45 | 9.09 | 36.80 | 57.41 | 5.79 |
| 60/40[10A] | 54.55 | 36.36 | 9.09 | 46.05 | 47.90 | 6.04 |
| 70/30[10A] | 63.64 | 27.27 | 9.09 | 56.14 | 37.54 | 6.31 |
| 80/20[10A] | 72.73 | 18.18 | 9.09 | 67.18 | 26.21 | 6.61 |
| 90/10[10A] | 81.82 | 9.09 | 9.09 | 79.31 | 13.75 | 6.94 |
| 50/50[15A] | 43.48 | 43.48 | 13 | 35.76 | 55.79 | 8.45 |
| 60/40[15A] | 52.17 | 34.78 | 13 | 44.70 | 46.50 | 8.80 |
| 70/30[15A] | 60.87 | 26.09 | 13 | 54.43 | 36.39 | 9.18 |
| 80/20[15A] | 69.57 | 17.39 | 13 | 65.03 | 25.37 | 9.60 |
| 90/10[15A] | 78.26 | 8.70 | 13 | 76.65 | 13.29 | 10.06 |
| 50/50[2D] | 49.02 | 49.02 | 1.96 | 38.78 | 60.51 | .71 |
| 60/40[2D] | 58.82 | 39.22 | 1.96 | 48.65 | 50.61 | .74 |
| 70/30[2D] | 68.63 | 29.41 | 1.96 | 59.46 | 39.76 | .78 |
| 80/20[2D] | 78.43 | 19.61 | 1.96 | 71.35 | 27.83 | .82 |
| 90/10[2D] | 88.24 | 9.80 | 1.96 | 84.49 | 14.65 | .86 |
| PAA[5D] | 0 | 95.24 | 4.76 | 0 | 98.55 | 1.45 |
| 50/50[5D] | 47.62 | 47.62 | 4.76 | 38.37 | 59.87 | 1.76 |
| 60/40[5D] | 57.14 | 38.10 | 4.76 | 48.11 | 50.05 | 1.84 |
| 70/30[5D] | 66.67 | 28.57 | 4.76 | 58.77 | 39.30 | 1.93 |
| 80/20[5D] | 76.19 | 19.05 | 4.76 | 70.49 | 27.49 | 2.02 |
| 90/10[5D] | 85.71 | 9.52 | 4.76 | 83.41 | 14.46 | 2.13 |
| PMMA[5D] | 95.24 | 0 | 4.76 | 97.76 | 0 | 2.24 |
| 50/50[7.5D] | 46.51 | 46.51 | 6.98 | 38.04 | 59.35 | 2.62 |
| 50/50[8.5D] | 46.08 | 46.08 | 7.83 | 37.90 | 59.14 | 2.95 |

*C.L.A.: Cross-linking agent used, A = AMA or D = DEGDMA.

The homopolymer samples are designated by the polymer name (PMMA or PAA) followed by a number representing the volume of the crosslinker added to 100 ml of monomer and a letter representing the type of crosslinking agent used (A for AMA and D for DEGDMA). In a similar fashion, the copolymer samples are designated by the ratio of MMA/AA monomers in the monomer mix followed by a number representing the volume of crosslinking agent added to 100 ml of the monomer mix and a letter representing the type of crosslinking agent used. The exact volumetric ratios and the corresponding molar ratios of these samples are also provided in Table 2. All samples synthesized exhibited high levels of transparency and appeared to be homogeneous having no noticeable cloud spots or segregations at the macroscopic level. While pure PMMA samples were colorless, pure PAA samples were dark-yellow. The copolymer samples appeared yellow and the intensity of the color increased with the amount of AA in the copolymer. In addition, it was observed that the color contrast described above was evident only following the final post-curing cycle.

It has been reported that AMA is a fairly good crosslinker for PAA (Greenberg et al., 1987, supra; El Basty et al., 1983, J. Dental Res. 62:733; Sharda, 1995, Ph.D. Thesis, Drexel University, Philadelphia, Pa.) and a relatively weak crosslinker for PMMA (Ding et al., 1991, J. Polymer Sci. Part B: Polymer Physics 29:1035). It has also been reported that DEGDMA is a better crosslinker for PMMA than is AMA (Ding et al., 1991, supra). It was therefore important to examine the effectiveness of both AMA and DEGDMA as crosslinking agents for PMMA, PAA and poly(MMA-AA) copolymer samples.

The initial study of crosslinker efficiencies was conducted in a series of dissolution/swelling tests on pure PMMA and PAA polymer as well as 50/50 poly(MMA-AA) copolymer samples synthesized with and without crosslinkers. The solvents used were an aqueous solution of NaOH in deionized water (0.5 g/100 ml) for PAA and a mixture of Toluene/Acetone (4:1 by volume) for PMMA (Xu et al., 1994, J. Polymer Sci. Part A: Polymer Chemistry 32:2803; Kowalczul et al., 1994, Macromolecules 27:572). As expected, PAA and PMMA samples synthesized without AMA or DEGDMA dissolved completely in their corresponding solvents while samples containing AMA or DEGDMA exhibited varying degrees of swelling depending on the amount of crosslinker used. Similarly the 50/50 copolymer samples synthesized without either crosslinker dissolved completely in both solvents while exhibiting varying degrees of swelling upon inclusion of AMA or DEGDMA.

The results of these tests provide evidence that both AMA and DEGDMA are effective crosslinking agents for the MMA/AA copolymer and also provide an assessment of the minimum amounts of AMA or DEGDMA which are required to obtain effective crosslinking. In general, it was found that 2% mol of AMA or 1% mol of DEGDMA was sufficient to obtain typical swelling behavior in either system without any indication of dissolution. Furthermore, the complete dissolution of the 50/50 non-crosslinked copolymer in both solvents is a clear indication that the copolymer is a true copolymer not a mixture of two homopolymers.

Figure 2:
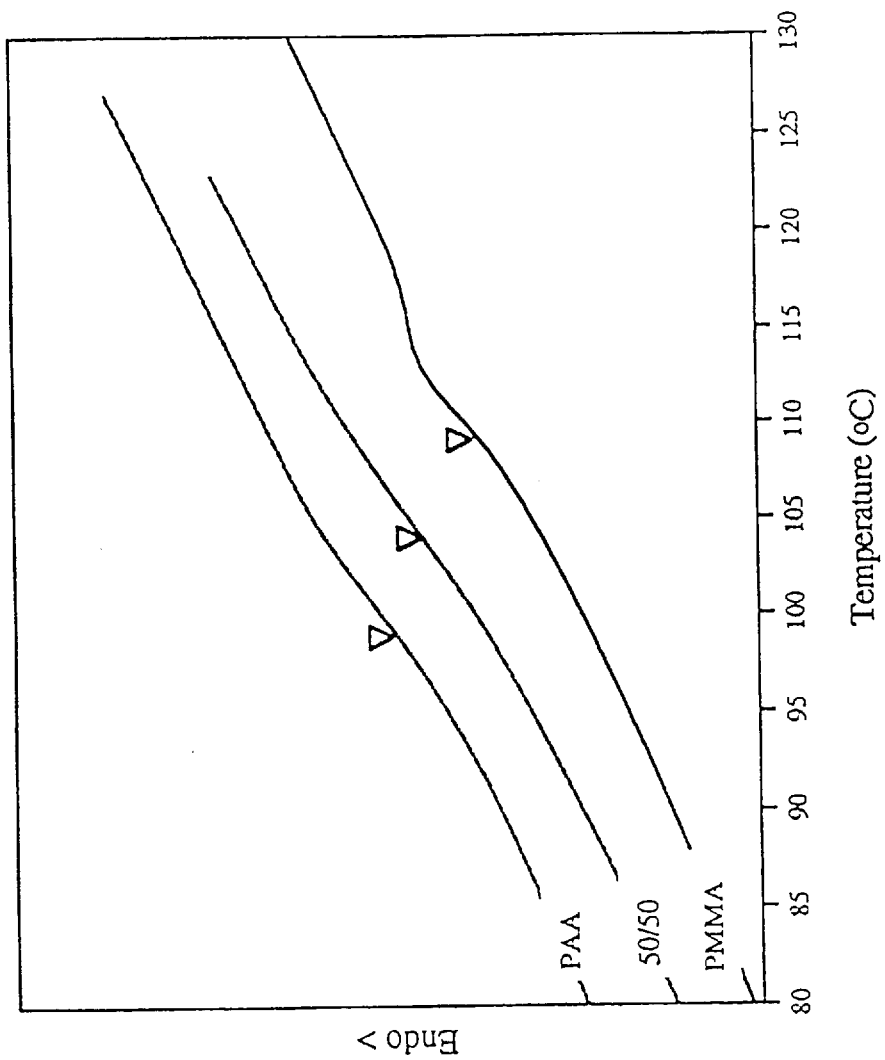
FIG. 2 is a graph depicting differential scanning calorimetry (D.S.C.) traces of non-crosslinked polyacrylic acid (PAA) polymethyl methacrylate (PMMA) and 50/50 polymer.

Differential scanning calorimetry (D.S.C.) was used to measure the glass transition temperatures (Tg) of the synthesized samples. It is important for the present application that the Tg of the formed copolymer is sufficiently high such that the copolymer cannot soften at normal or even elevated body temperatures. In FIG. 2 there is shown the normalized D.S.C. traces for PMMA, PAA and 50/50 poly(MMA-AA) polymer samples obtained using Perkin-Elmer thermal analysis system-Series 7. All traces shown are second runs on samples containing no cross-linking agent and obtained at a heating rate of 10° C./minute. It has been reported (Turner et al., 1986, Polymer 27:1619) that the first D.S.C. runs in polymers containing hydrophilic groups may exhibit a peak resulting from absorbed water molecules. This peak was found to disappear in second runs. Argon was used as the sweeping gas and all samples weighed about 5 mg. All glass transition temperatures reported in the present study were estimated from thermographs using a built-in Perkin-Elmer TAS7 software package. The traces indicate that the glass transition temperatures for the synthesized PAA and PMMA non-crosslinked homopolymers are 98° C. and 108° C., respectively. A single transition temperature of 1030° C was detected for the 50/50 copolymer samples. These results confirm the formation of a single phase in the synthesized copolymer. Furthermore, the value of the Tg measured for the copolymer is in good agreement with the expected value computed from the Tg's of the constituent homopolymers using any one of relations used in current literature such as the weighted average rule (by weight fractions) or the inverse weighted average rule. For example, the inverse weighted average rule, $$\frac{1}{T_g} = \frac{W_1}{T_{g1}} + \frac{W_2}{T_{g2}}, \tag{1}$$

where $W_1$ and $W_2$ are the weight fractions of the copolymer constituents, and $Tg_1$ and $Tg_2$ are their respective glass transition temperatures in K, provides an estimate of 105° C. which is in good agreement with the measurement.

Figure 3:
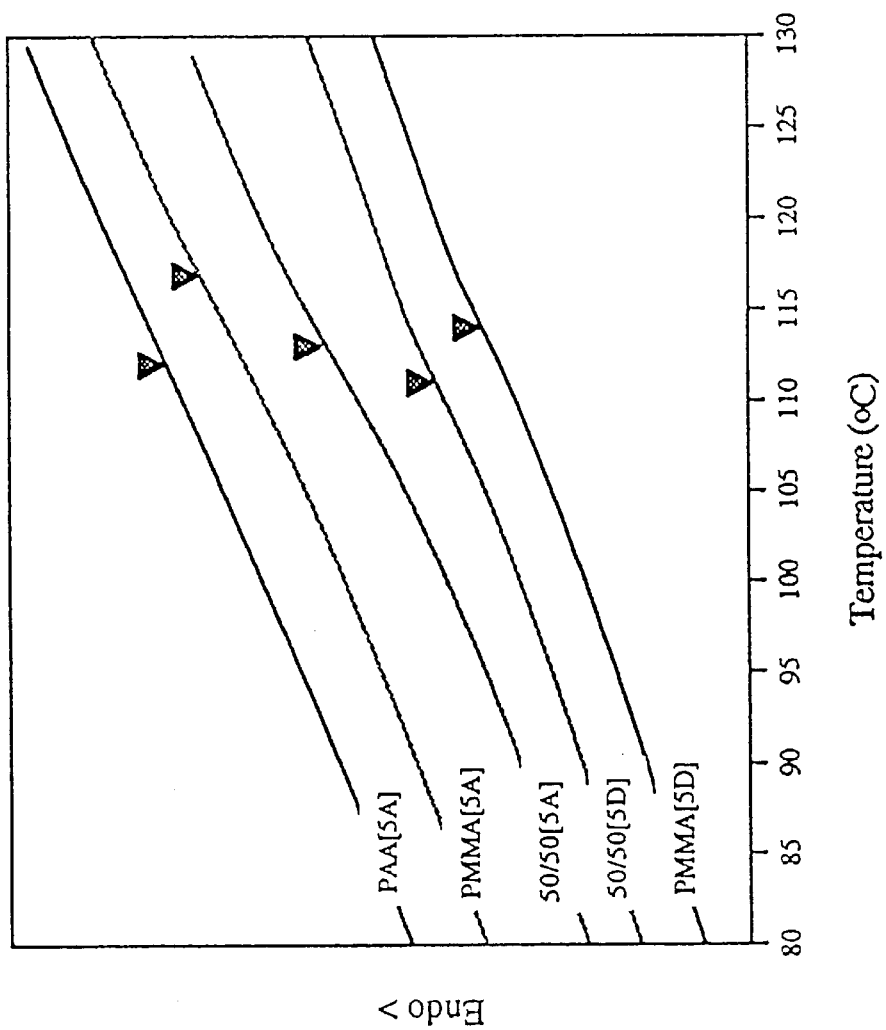
FIG. 3 is a graph depicting D.S.C. traces of crosslinked PAA, PMMA and 50/50 copolymer.

In the case of crosslinked copolymers, the analysis of the glass transition behavior becomes complicated (Weber et al., 1988, Polymer 29:1071). It is generally known in crosslinked systems that the softening temperature increases with crosslink density as a consequence of reduced segmental mobility (Weber et al., 1988, supra; Ward, 1971, Mechanical Properties of Solid Polymers, Wiley, N.Y.). In addition, the glass transition behavior becomes less evident with crosslinking as a consequence of the reduction of the linear portion in the polymer structure. Both effects can be seen by comparing the D.S.C. traces of the crosslinked copolymer samples shown in FIG. 3 with those shown in FIG. 2 for the non-crosslinked copolymers. Both figures are drawn to the same horizontal and vertical scale for comparison purposes and some of the traces are shifted vertically to avoid overlapping. The Tg values obtained from these measurements are summarized in Table 3 and are reproducible within 2 degrees of each other.

TABLE 3

SUMMARY OF THE GLASS TRANSITION TEMPERATURES OF SYNTHESIZED COPOLYMER SAMPLES WITH DIFFERENT COMPOSITIONS AND DIFFERENT AMOUNTS OF CROSS-LINKING AGENTS

| SAMPLE | Tg (°C.) |
| --- | --- |
| PAA[0] | 98 |
| PMMA[0] | 108 |
| 50/50[0] | 103 |
| PAA[5A] | 111 |
| PMMA[5A] | 116 |
| PMMA[5D] | 114 |
| 50/50[5A] | 112 |
| 50/50[5D] | 111 |

Figure 4A:
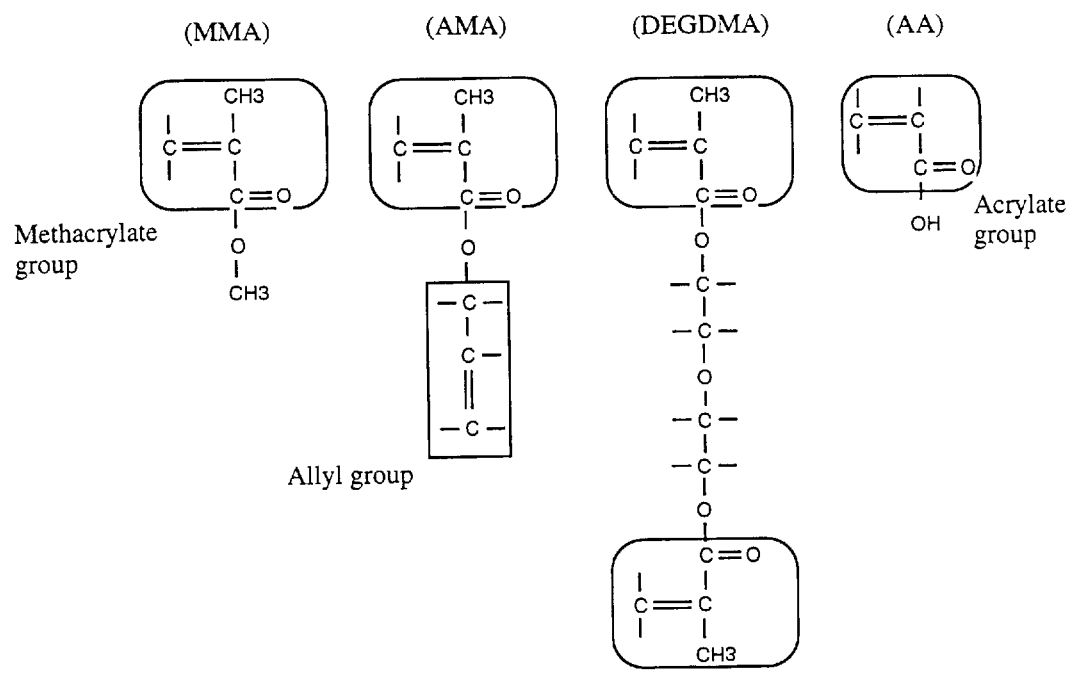
FIG. 4(a) depicts the chemical structure of the monomers used in the present invention showing the reactive groups involved in the polymerization process.

Despite the difference in their hydrophilic/hydrophobic nature, MMA and AA monomers have similar reactivities (Brandrup et al., 1989, Polymer Handbook (3rd Edition) II-164, Wiley, N.Y.). The same applies to the methacrylate functional group in AMA and DEGDMA (see FIG. 4(a)). It is assumed, therefore, that the three monomer units (MMA, AA, and the crosslinker) react in a random fashion depending on their molar ratios to form the main copolymer chains. Since all polymerization reactions were carried essentially to 100% conversion, the final composition of the copolymer is assumed to be the same as the initial ratios used. To confirm complete conversion, synthesized copolymer samples were crushed into a powder form and were incubated in a vacuum oven for 6 hours at 100° C. No detectable weight loss was observed indicating that no unreacted monomers remained in the copolymer composition.

Crosslinking between polymer chains is achieved by the extra functional groups in both crosslinking agents. In the case of AMA, this crosslinking is accomplished via the allyl functional groups which are known to have lower reactivities than acrylate and methacrylate groups in AA, MMA, and DEGDMA monomers (Ding et al., 1991, supra; Higgins et al., J. Polymer Sci. Part A-1: Polymer Chemistry 6:3007). This explains, in part, the relatively high amounts of AMA required to achieve effective crosslinking. In addition, the results of swelling measurements establish that this crosslinking is more evident after the post-curing heat treatment cycle.

Figure 4B:
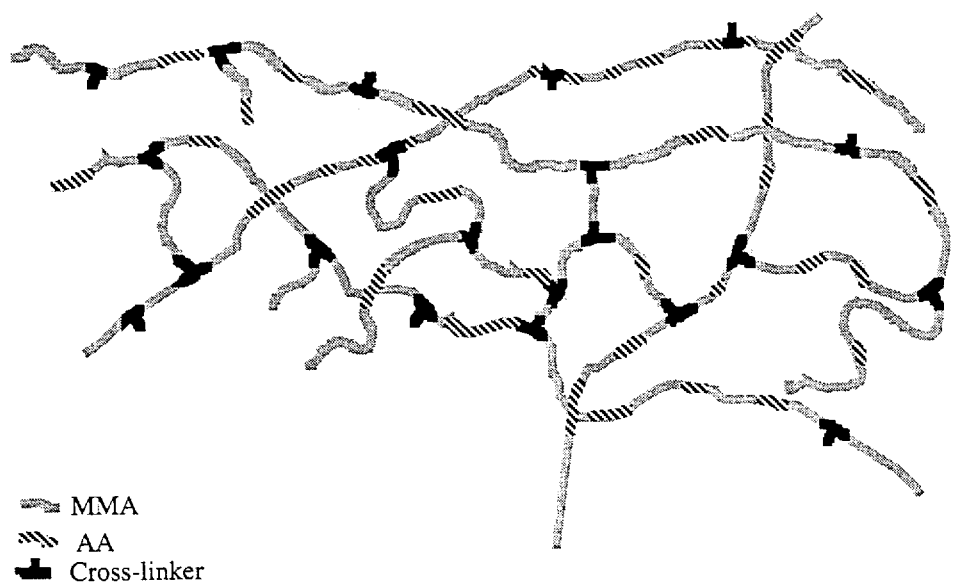
FIG. 4(b) is a diagram of a simplified model of the structure of the synthesized crosslinked copolymer indicating methyl methacrylate (MMA) and acrylic acid (AA) components with crosslinks.

Based on the above discussion, and supported by the D.S.C. and the dissolution/swelling observations, the model shown in FIG. 4(b) was constructed to represent the synthesized crosslinked copolymer. Notice that the MMA and AA units are distributed randomly along the chains and some crosslinker units are shown as not participating in the crosslinking process.

Swelling Behavior

Thin circular discs (13 mm diameter and 1 mm thickness) were cut out of the bulk samples using a diamond saw, washed with methanol and dried in an oven for 6 hours at 80° C. before they were fully immersed in excess saline solution (0.9 g/100 ml NaCl, Fisher Scientific, Pittsburgh, Pa.) for 200 hours at 25° C. The swollen discs were removed from the solvent at various times, surfacedried using filter paper and weighed using a digital scale with an accuracy of ±.0001 g. The exact dimensions of the samples were also measured using a digital micrometer with an accuracy of ±.001 mm. The percentage weight gain, %W, of the swollen samples at any instant during swelling is computed as $$\% W = \left( \frac{W_t - W_o}{W_o} \right) \times 100, \tag{2}$$

where Wt and Wo are the weights of the disc at zero (the dry state), respectively. As swelling reaches equilibrium, %W approaches the saturated swelling otherwise known as the equilibrium solvent content, %Weq. Similarly, the percentage change in volume, %V, of the swollen samples is given by $$\% V = \left( \frac{V_t - V_o}{V_o} \right) \times 100, \tag{3}$$

which can be calculated from %W assuming volume additivity of the polymer and the solvent in the swollen samples using $$\% V = \left( \frac{\rho_m}{\rho_s} \right) \% W, \tag{4}$$

where $\rho m$ and $\rho s$ are the densities of the dry copolymer and the solvent, respectively. All swelling measurements reported in this study are based on weight gain measurements (%W) as obtained from Equation 2. Nevertheless, the validity of Equation 4 in calculating the percentage change in volume from the percentage change in weight was confirmed experimentally (by comparison with Equation 3) for several sets of measure The primary objective of the swelling experiments was to study the influence of the hydrophilic/hydrophobic ratios and the amount and type of crosslinker on the swelling behavior of the synthesized copolymer in saline solution. The different compositions of the samples used in the swelling measurements are included in Table 2. Three samples of each composition were used in each set of measurements and the scatter within each set was very minimal (within 3% of the average weight gains).

Effect of Hydrophilic/Hydrophobic Ratio

Figure 5:
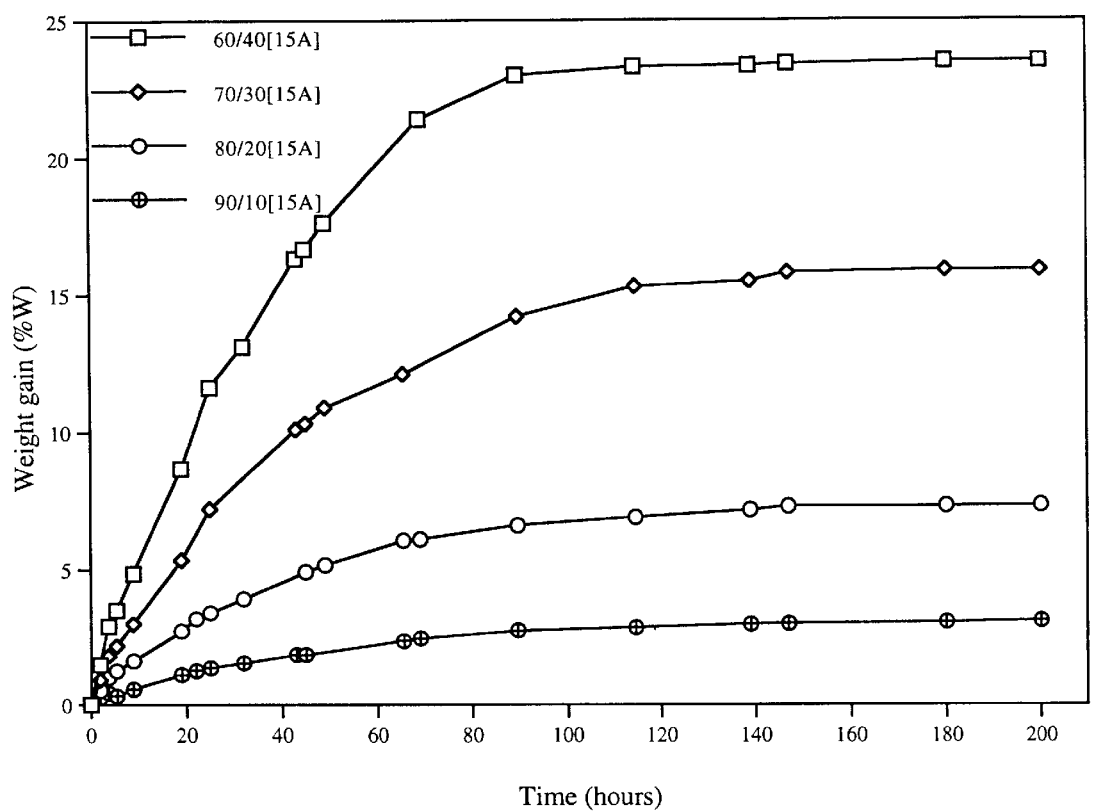
FIG. 5 is a graph depicting the effect of the AA content on the swelling behavior of AMA crosslinked polymer.

In FIG. 5 there is shown typical swelling curves generated for a series of swelling measurements conducted on samples containing varying ratios of MMA/AA but identical amounts (% of total volume) of AMA. These curves clearly show the significant effect of increasing the relative amount of AA in increasing the swelling levels of the synthesized copolymer. The copolymers in this figure exhibit similar time-scales for approaching equilibrium. Generally, half of the saturated weight gain was achieved in the first 24 hours after immersion, and the saturation weight gain was reached in about 100 hours. Further swelling after the first 100 hours was very slow and essentially ceased after about 200 hours. No noticeable effect of the MMA/AA ratio on the swelling time-scale described above was observed.

Figure 6:
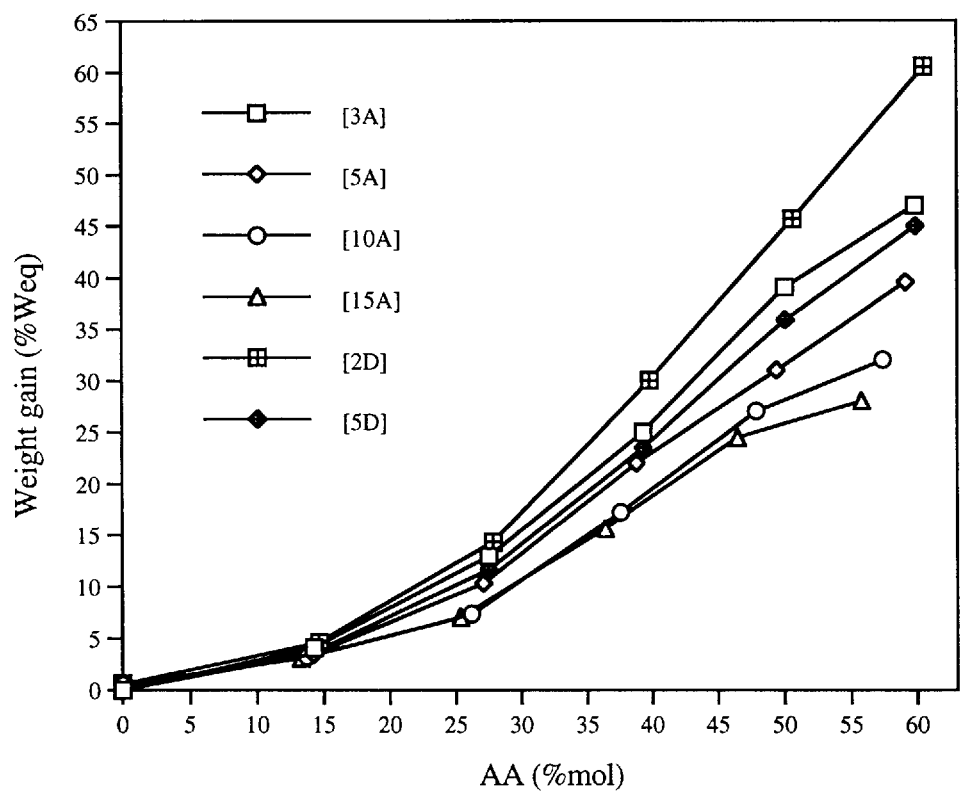
FIG. 6 is a graph depicting the effect of the AA content on saturated swelling levels of the copolymer.

Similar results to those described above were obtained from samples using DEGDMA as the crosslinker, except for the values of saturated swelling. In FIG. 6 there is shown the effect of the relative amount of AA (%mol) on the saturated swelling values for different amounts of the two crosslinkers used in this study. Notice that each solid line represents one series of swelling measurements on samples containing varying ratios of MMA/AA but identical amounts of the crosslinker (%vol). All curves shown in FIG. 6 indicate a monotonic increase in saturated weight gain with increase in the relative amount of AA in the copolymer. Furthermore, this relationship is observed to be fairly linear for moderate amounts of AA (greater than 25% mol and less than 50% mol) in the copolymer. Some nonlinearity is also observed in all these curves, especially at low %mol of AA in the copolymer.

Effect of Crosslinker

Figure 7:
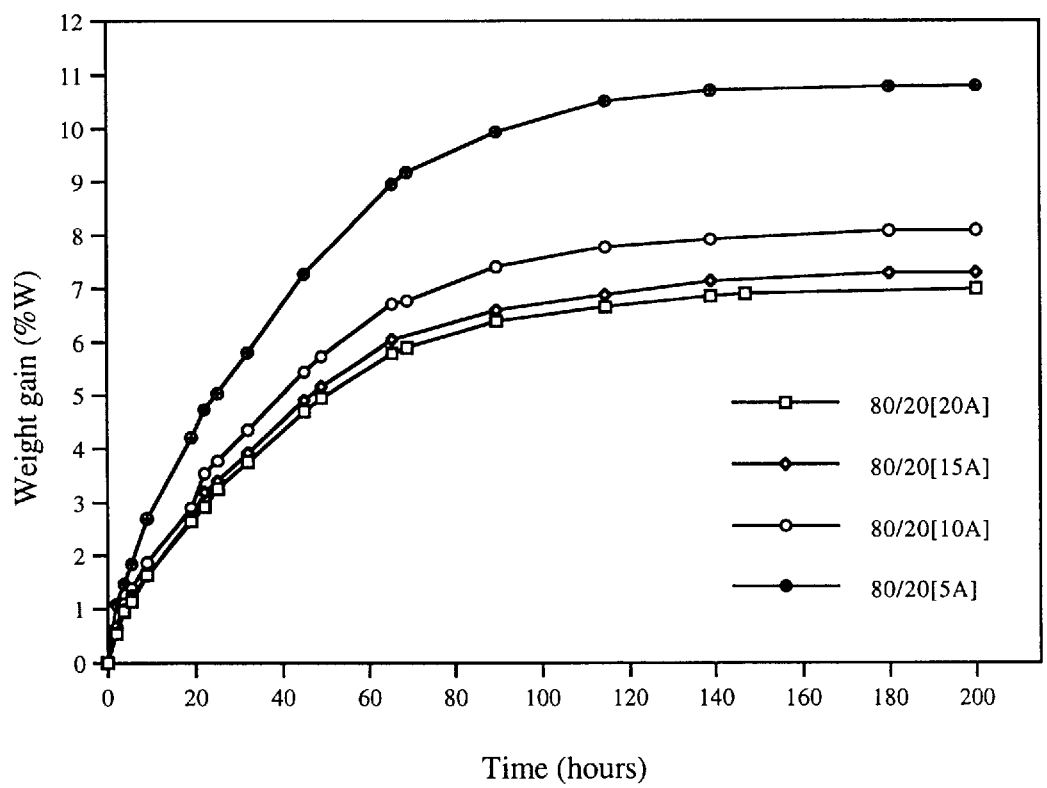
FIG. 7 is a graph depicting the effect of the amount of crosslinking agent (AMA) on the swelling behavior of an 80/20 crosslinked copolymer.

The swelling curves obtained from a series of samples containing identical MMA/AA ratios (80%/20%) but varying amounts of AMA (5%–20%) are shown in FIG. 7. It is apparent from FIG. 7 that increasing the ratio of crosslinker reduces the saturated swelling levels of the copolymer without affecting the time needed to reach saturation.

Figure 8:
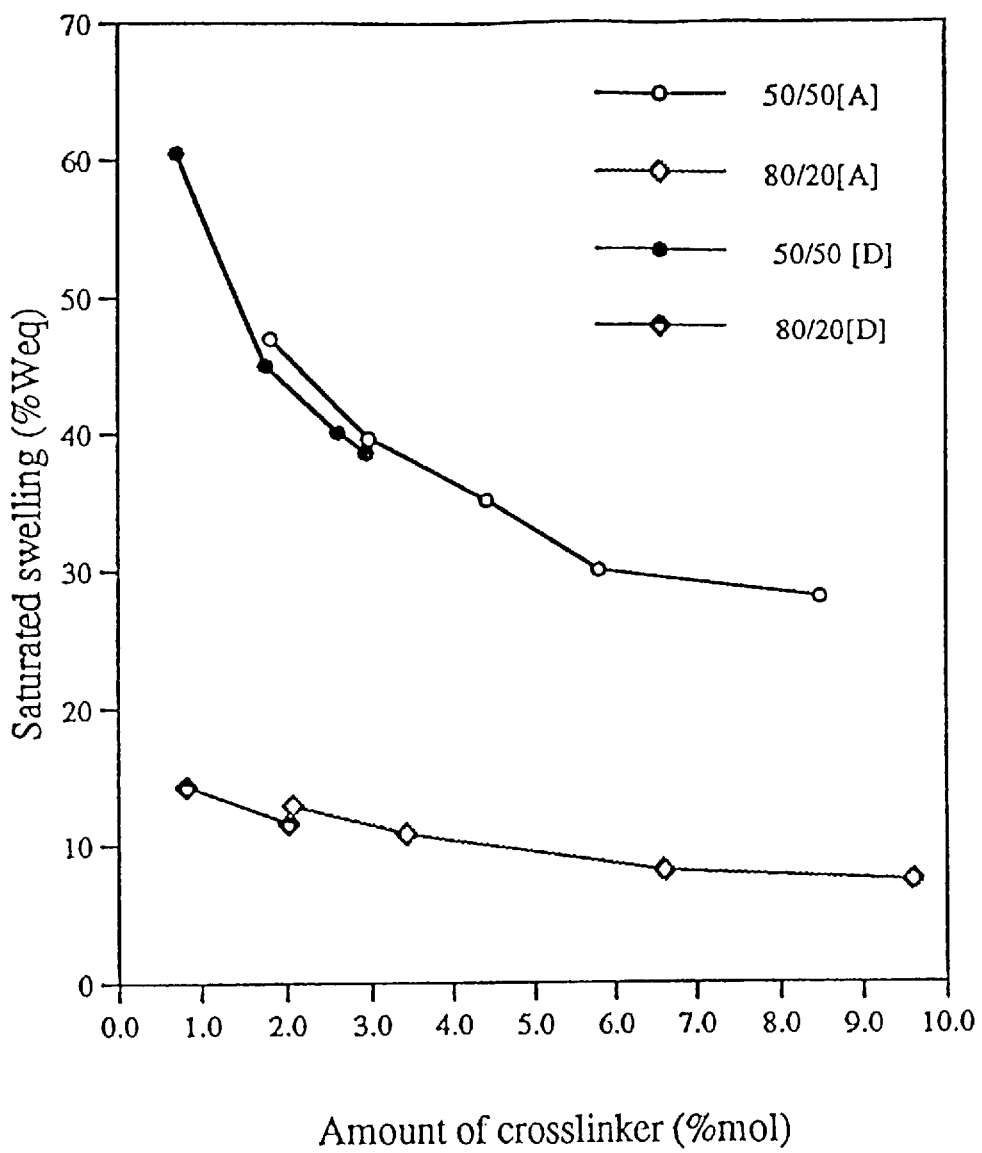
FIG. 8 is a graph depicting the effect of the amounts of the two crosslinking agents on saturated swelling of the copolymer.

To further investigate the effectiveness of both crosslinkers in controlling the swelling behavior of the copolymer, the saturated swelling measurements were plotted against the molar percentages of crosslinker for both AMA and DEGDMA, as shown in FIG. 8. Notice that each solid line in this case represents a series of swelling measurements on samples containing fixed ratio of MMA/AA and varying amounts of crosslinker. All plots exhibit an asymptotic decrease in the saturated swelling levels with the % mol of crosslinker. No significant reduction in saturated swelling was obtained when the amount of AMA was increased beyond 6 mol%. Furthermore, it can be seen from FIG. 8 that for the same molar percentages, DEGDMA is only slightly more effective in crosslinking the synthesized copolymer than is AMA, as indicated by the slightly lower saturated swelling values obtained at identical molar percentages of both crosslinkers. However, when the saturated swelling levels are plotted for constant volume ratio as shown in FIG. 6 (instead of the molar ratio used in FIG. 8), it can be seen that AMA is slightly more effective than DEGDMA.

Diffusion Measurements

In addition to the equilibrium degree of swelling, the rate at which equilibrium is reached and the transport mechanism of swelling are of great importance in the intended application. In the simplest case, where the transport mechanism is Fickian, the rate of approaching equilibrium is characterized by the diffusion coefficient, D. The value of D can be obtained from graphing the degree of saturation ( FW/%Weq) against $\sqrt{t}$/L, where t is the time and L is the initial thickness of the specimen. The linearity of the initial portion of the plot (%W/%Weq <0.6) is an indication of Fickian diffusion mechanism and the diffusion coefficient can then be determined from the slope of the linear portion using $$\frac{\%W}{\%Weq} = \sqrt{\frac{D}{16}\pi} \, \frac{\sqrt{t}}{L} \quad (5)$$

Figure 9A:
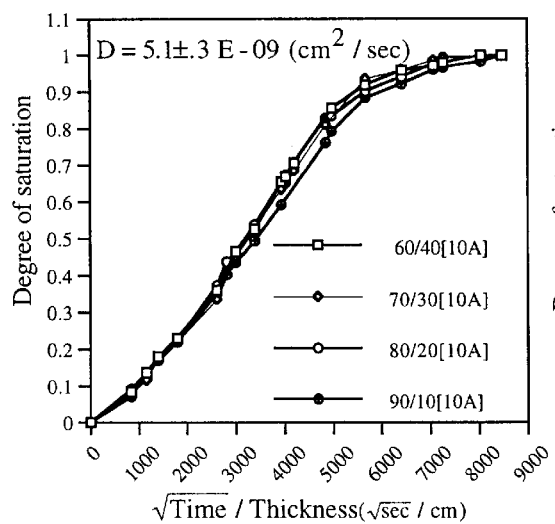
FIG. 9(a) is a graph depicting the effect of AA content on the diffusion coefficient (D).
Figure 9B:
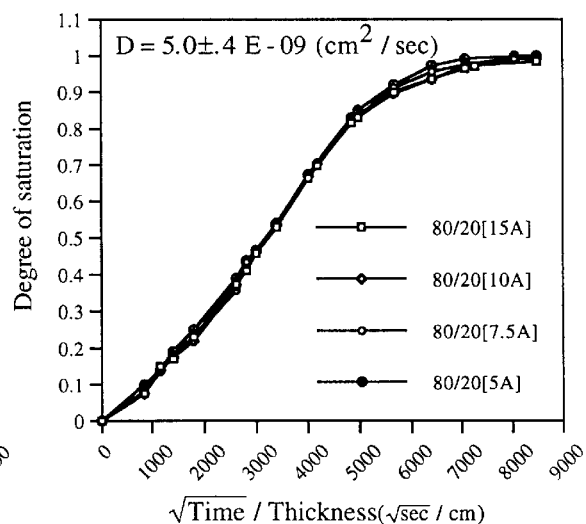
FIG. 9(b) is a graph depicting the effect of the amount of crosslinking agent on the diffusion coefficient (D).

It has been reported that both the amount of crosslinker and/or the hydrophobic/hydrophilic balance can have a significant effect on the absorption rate and/or mechanism in some crosslinked polymer networks (Ahmad et al., 1994, Polymer 35:1997; Yoa et al., 1994, J. Polymer Sci. Part A: Polymer Chemistry 32:1213; Takashi et al., 1994, Macromolecules 27:947). FIG. 9 shows the diffusion plots generated for two series of swelling measurements in which the amount of crosslinker and the MMA/AA ratio are systematically varied. It is apparent from these figures that all curves are virtually identical and overlap for the major part of the swelling history. This clearly indicates that neither the amount of the crosslinker nor the hydrophobic/hydrophilic ratio has a significant effect on the sorption rate in the synthesized polymer. In addition, all curves exhibit a high degree of linearity in the initial portions (%W/%Weq <0.5) indicating that the diffusion mechanism is Fickian. The values of D obtained at room temperature for all samples in our study were in the range of $4.7–5.4\times10^{-9}$ cm$^2$/second. It should be noted that these values are roughly an order of magnitude higher than those reported for epoxy resins (El-Sa's ad et al., 1990, J. Material Sci. 25:3577) and at least an order of magnitude lower than those for highly swellable hydrogels (Ahmad et al., 1994. supra; Kabra et al., 1991, J. Applied Polymer Sci. 42:2409; Firestone et al., 1988, Polymer Communications 29:204).

Effect of Temperature

Figure 10:
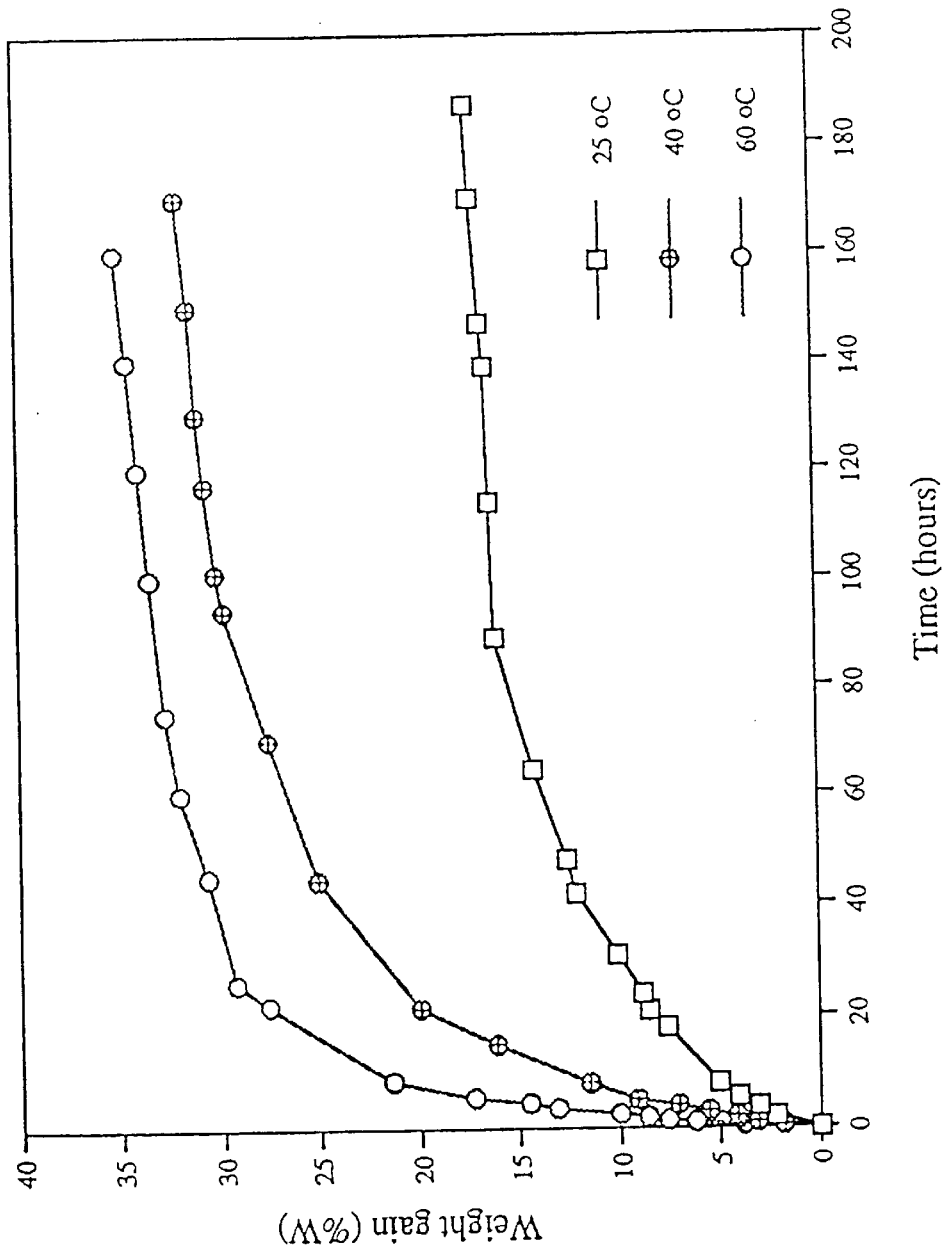
FIG. 10 is a graph depicting the effect of temperature on the swelling behavior of 70/30 [10A] copolymer.
Figure 11:
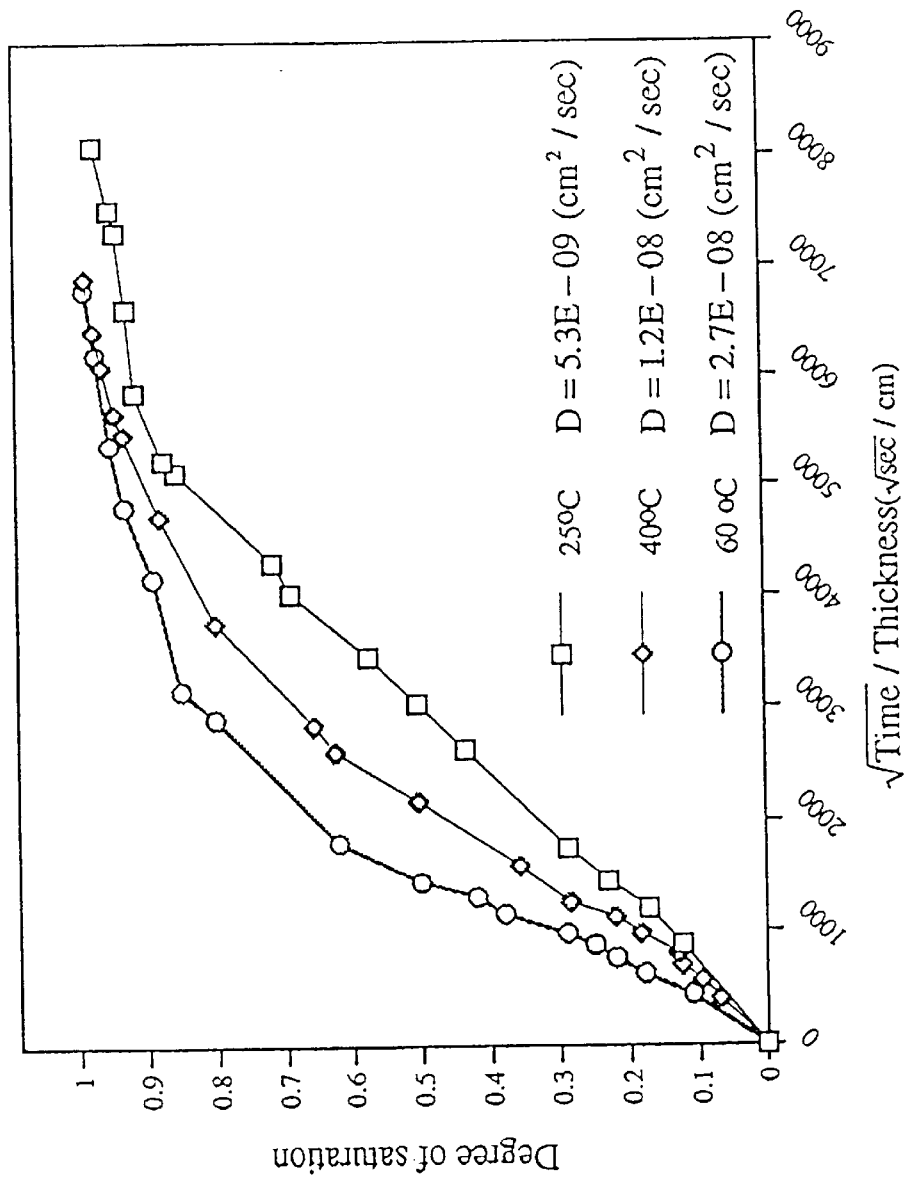
FIG. 11 is a graph depicting the effect of temperature on the diffusion coefficient (D) in 70/30 [10A] copolymer.

The effect of temperature on the swelling behavior of the synthesized copolymer was examined in three sets of samples having an MMA/AA composition of 70/30 with 10% AMA crosslinking agent at temperatures of 25° C., 40° C., and 60° C. The swelling curves are shown in FIG. 10 and the corresponding diffusion plots are shown in FIG. 11. The results indicate that raising the temperature of the swelling media has a significant effect on both the saturated swelling and the absorption rate (characterized by the diffusion coefficient). The diffusivities (D) of the swollen samples derived from the initial slopes of the curves obeyed an Arrhenius behavior which can be represented by the expression $$D = .0451\exp\left(\frac{-39580}{RT}\right) (\text{cm}^3/\text{sec}) \quad (6)$$

where, R is the gas constant, 8.31 J/mol-K, and T is the absolute temperature in K.

It can also be seen from FIG. 10 that the saturated swelling increases with temperature in the range of temperatures tested here. Furthermore, the increase in saturated swelling level between 40° C. and 60° C. is fairly small compared to the increase between 25° C. and 40° C.

Studies on the Copolymer Plus Fiber

Synthesis of Materials

The copolymer was synthesized as described above, except that the relative amounts of MMA and AA monomers were varied to yield materials having different swelling capacities (Table 4). Thus, a variety of composite materials were produced using crosslinked poly(MMA-AA) as the matrix (see Table 4). Primarily, two types of fibers were used as the reinforcement. These were AS-4 carbon (graphite) fibers (Hercules Inc., Salt Lake City, Utah) and Kevlar-49 fibers (E. I. Dupont de Nemours & Co., Wilmington, Del.). Both fibers have been widely used as reinforcement in polymeric composites for load-bearing composite applications, which include some bioimplant applications (Spector et al., 1978, Biomedical Materials Research Symp. Trans. 2:124); Sclippa et al., 1973, J. Biomed. Materials. Res. 7:59; Park et al., 1992, Biomaterials: An Introduction, 2nd Edition, Plenum Press, New York).

TABLE 4

LIST OF POLYMER AND COMPOSITE MATERIALS SYNTHESIZED FOR THIS STUDY ALONG WITH THEIR MEASURED DENSITIES

| SAMPLE | MATRIX COMPOSITION (MMA/AA) | REIN-FORCE-MENT | FIBER VOLUME FRACTION | DENSITY (g/cc) |
|---|---|---|---|---|
| COPOLY1 | 90/10 | None | 0.00 | 1.17 |
| COPOLY2 | 80/20 | None | 0.00 | 1.20 |
| COPOLY3 | 70/30 | None | 0.00 | 1.22 |
| COPOLY4 | 60/40 | None | 0.00 | 1.25 |
| UNIDIR-C | 80/20 | Uniaxial-Carbon | 0.30 | 1.35 |
| UNIDIR-K | 80/20 | Uniaxial-Kevlar | 0.30 | 1.26 |
| BRAID-C1 | 80/20 | Circular Braided & Uniaxial-Carbon | 0.43 (0.30 + 0.13) | 1.42 |
| BRAID-C2 | 60/40 | Circular Braided & Uniaxial-Carbon | 0.43 (0.30 + 0.13) | 1.46 |

Figure 12:
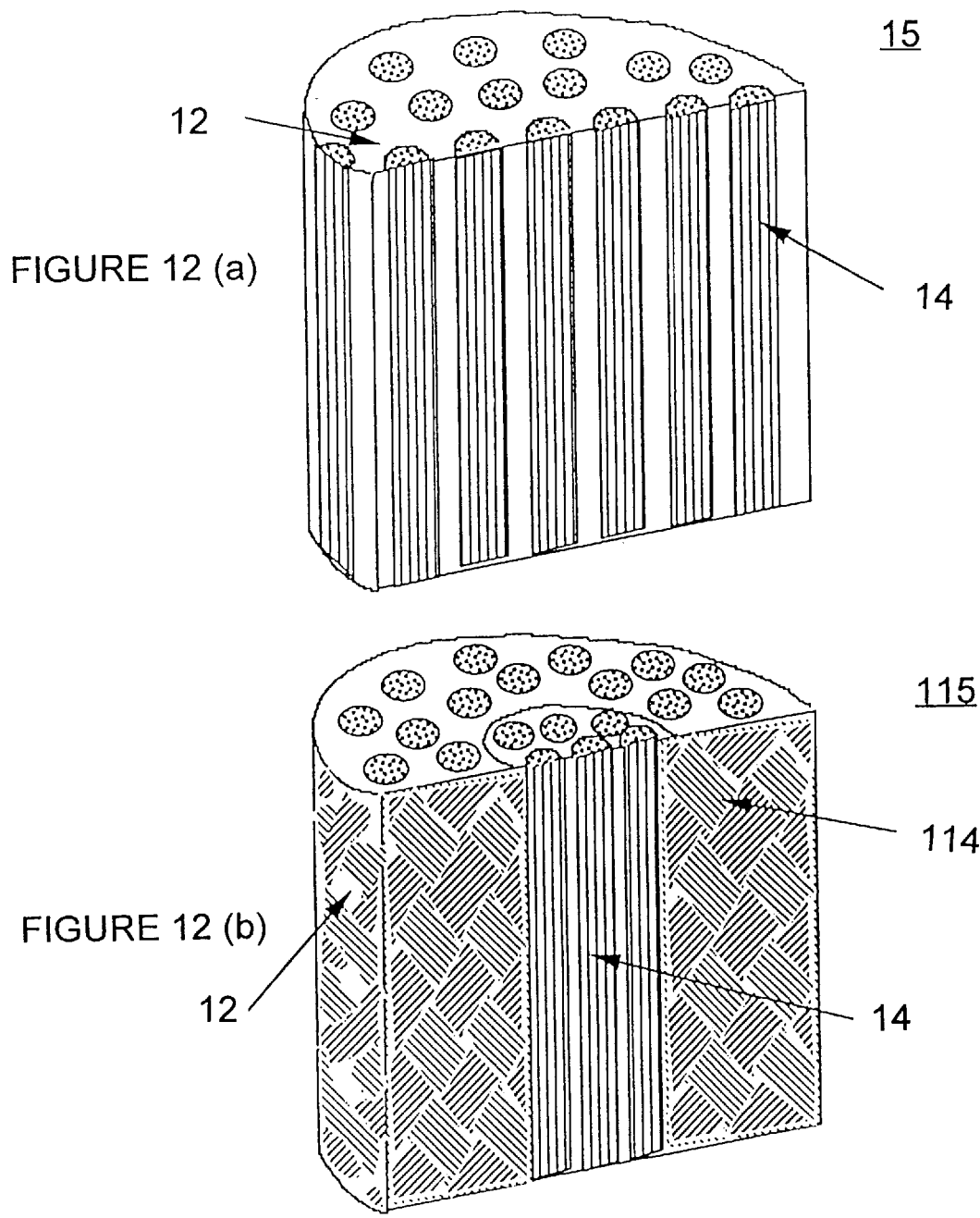
FIG. 12(a) is a schematic diagram of the longitudinal cross-section in a synthesized, unidirectional composite sample.
FIG. 12(b) is a schematic diagram of the longitudinal cross-section in a synthesized, circular, cross-braided composite.

In the present study, composite samples with two different fiber architectures were produced (FIG. 12). The first set of samples 15 were produced having all of the fibers 14 oriented in one direction (axially) through the MMA/AA matrix 12 and are referred to as unidirectional composites (FIG. 12a). It is well known that unidirectional composites exhibit good mechanical properties (e.g., stiffness and strength) in the fiber direction, but are relatively weak in directions transverse to the fibers. Also produced were three-dimensionally braided composites 115. Three-dimensional circular braids 114 (Wang et al., 1995, Composite Science and Technology 53:213; Ko, 1989, Ceramic Bulletin 68:(No.2) 401) of AS-4 carbon fiber yarns were produced in the Fibrous Materials Research Laboratory at Drexel University, Pa., using a circular loom with 4-step 1X1 braiding procedure to provide a fiber-volume fraction of approximately 43% (13% of which are uniaxial directed fibers 14 in the core and 30% are braided fibers as shown in FIG. 12(b)). Since the fiber orientations in the braided composites are distributed in all directions (see FIG. 12(b)), the braided composites 115 yield more balanced properties. The properties in the axial direction are relatively lower compared to the unidirectional composites, whereas the transverse properties are significantly higher. The braided composites also have significantly higher damage tolerance (Ko, 1989, supra; Chou et al., 1989, Textile Structure Composites, Elsevier Science Publishers, Amsterdam, 129–171). For producing the composite samples, the reinforcement was placed in the test tubes before the monomer mixture was poured into the test tubes, and essentially the same procedure that is described herein for processing the copolymer was followed.

Both carbon and Kevlar fibers are considered to be biocompatible (Sharda, 1995, supra; Park et al., 1992, supra; Storey et al., 1993, Polymer Composites 14:No 1), but not resorbable and long-term direct contact between these fibers and tissue is undesirable (Storey et al., 1993, supra). Therefore, when synthesizing the copolymer, 100% conversion must be achieved in the matrix during polymerization in order to prevent the matrix from dissolving after implantation thereby exposing the fibers. The measured glass transition temperature of the synthesized poly (MMA-AA) matrix is about 110° C. which is well above the biological temperature of the human body, further ensuring that the implant will remain rigid after implantation.

A detailed microscopic investigation of the composite was conducted using Scanning Electron Microscopy (SEM) on synthesized composite samples containing both types of fibers in order to characterize the fiber/matrix interface and to investigate the influence of various processing and thermal effects on the synthesized composite.

Fiber matrix debonding is a frequently encountered problem in many polymeric composite systems which can seriously limit the usefulness of these composites especially in physiological environments. If considerable debonding occurs, rapid mechanical degradation follows and degradation products may be hazardous (Hench et al., 1982, "Biomaterials: An Interfacial Approach" Vol. 4 Academic Press, New York). Furthermore, debonding provides channels through which body fluids may come in contact with the fibers causing degradation. Degradation products may be transported away from the implant site causing problems elsewhere in the body. In many cases debonding is caused by the inherent thermodynamic and/or chemical incompatibility of the fiber surface and matrix studied. This is not likely to be the case when AS-4 carbon fibers are used because of the highly reactive functional groups on their surface introduced by surface treatment and coating by the manufacturer. In addition, the presence of pendant COOH, OH, and C=O functional groups on the synthesized copolymer chains is believed to improve adhesion with carbon fibers by forming hydrogen bonding and dipole/dipole interactions with similar groups on the coated fibers (Wu et al., 1995, Polymer Composites 16: No.4; King et al., 1993, Polymer Composites 14: No. 4; Ko et al., 1995, Polymer Composites 16: No. 3). Indeed, it was observed in the present study that few debonding sites were observed in the carbon reinforced composites. These debondings consistently occurred only after the final postcuring cycle, which is an indication that thermal effects (due to the differences in thermal expansion coefficients between matrix and fibers) caused the observed fiber/matrix debonding. The fiber/matrix debonding in the AS-4 carbon reinforced composites was substantially eliminated by slowing down the heating and cooling rates during post-curing.

Kevlar fibers have certain inherent advantages-for biomedical applications. Their organic nature, inertness, and excellent fracture toughness render these fibers a viable alternative to carbon or graphite fibers. There are two major defects which can be identified in Kevlar fibers embedded in the copolymer of the invention: (1) severe debonding at the fiber/matrix interface, and (2) fibrillation of the Kevlar fiber. These defects were present in all Kevlar reinforced composite samples produced in the present study and remained after all processing attempts to eliminate them. These defects are characteristic of Kevlar reinforced composites (Mobarakeh et al., 1996, Polymer Engineering and Science 36: No. 6778; Morgan et al., 1987, Polymer 28:340; Wang et al., 1993, J. Applied Polymer Sci. 48:121; Breznick et al., 1987, Polymer Communications 28:55). Unlike carbon fibers where several surface treatments and coating techniques have been successfully and commercially implemented to enhance their bonding characteristics, no effective surface treatment or coating technique, to date, has been found to consistently improve the adhesion characteristics of Kevlar fibers with a range of polymeric matrices.

Swelling Behavior

The free swelling behavior of the various materials produced in this study was characterized to determine the optimum range of monomer ratio (MMA/AA) for the use of the composite material for anchoring soft tissue to bone. When in bone, the implant is subjected to swelling which is constrained by the surrounding bone. Thus, the swelling behavior of the materials used in the present study is expected to be strongly dependent on the degree of constraint. Therefore, the actual degree of swelling achieved by the material in the implanted condition depends on its capacity to swell in the unconstrained (free) condition, the clearance between the implant and bone, and the magnitude of the swelling induced pressure at the bone-implant interface. Since the later two factors are determined by the design parameters in the actual application, what follows is a characterization only of the free-swelling behavior of the different materials useful in the present application. It should however be noted that free swelling provides an upper limit on the maximum swelling levels that can be achieved for the material, and a lower limit for its properties in the swollen state since higher swelling invariably leads to a higher loss of modulus and strength.

Cylindrical samples (about 5 mm diameter and 7 mm height) of the copolymer as well as the composite were immersed in saline solution to characterize their free swelling behavior. The percentage weight gain, %W, of the swollen samples at any instant during swelling was computed as before using formula (2). As swelling reaches equilibrium, %W approaches the saturated swelling level, Wsat, otherwise known as the equilibrium solvent content. Similarly, the percentage change in volume, %V, of the swollen samples was calculated using formula (3) which can be calculated from %W assuming volume additivity of the polymer and the solvent in the swollen samples using formula (4). All swelling measurements reported in this study were obtained as weight gain measurements (%W), and then converted to volumetric strains (%V). This approach was used because of our ability to measure weight changes with much higher precision (up to 0.01 mg) than volume changes.

Figure 13:
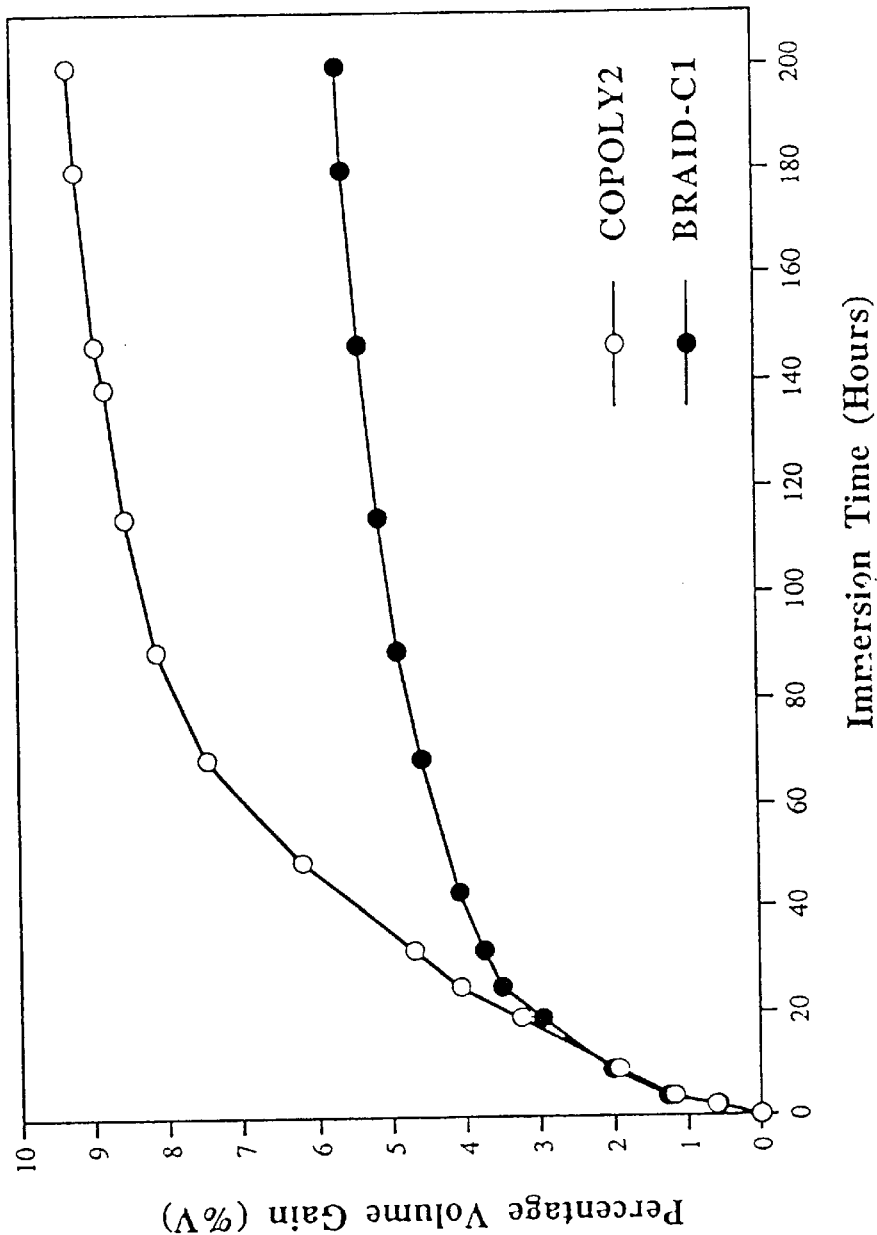
FIG. 13 is a graph depicting typical free-swelling curves for copolymer and circular braided composite samples containing a methyl methacrylate/acrylic acid (MMA/AA) ratio of 80/20.

In FIG. 13 there is shown typical free swelling curves obtained for the 80/20 copolymer (COPOLY2 in Table 4) and the circular braided composite of carbon fibers embedded in the 80/20 copolymer (BRAID-C1) in Table 4). It is observed that the introduction of the fibers results in a significant reduction in the saturated swelling strain of the material since the fibers apply an internal constraint on the swelling of the material, but has little influence on the swelling kinetics. That is, the two curves exhibit similar time-scales in approaching saturation. Generally, half of the saturated swelling strain was achieved in the first 24 hours after immersion, and saturation was reached in about 100 hours for the samples used in this study. Additional swelling after the first 100 hours was very slow and essentially ceased after about 200 hours.

Figure 14:
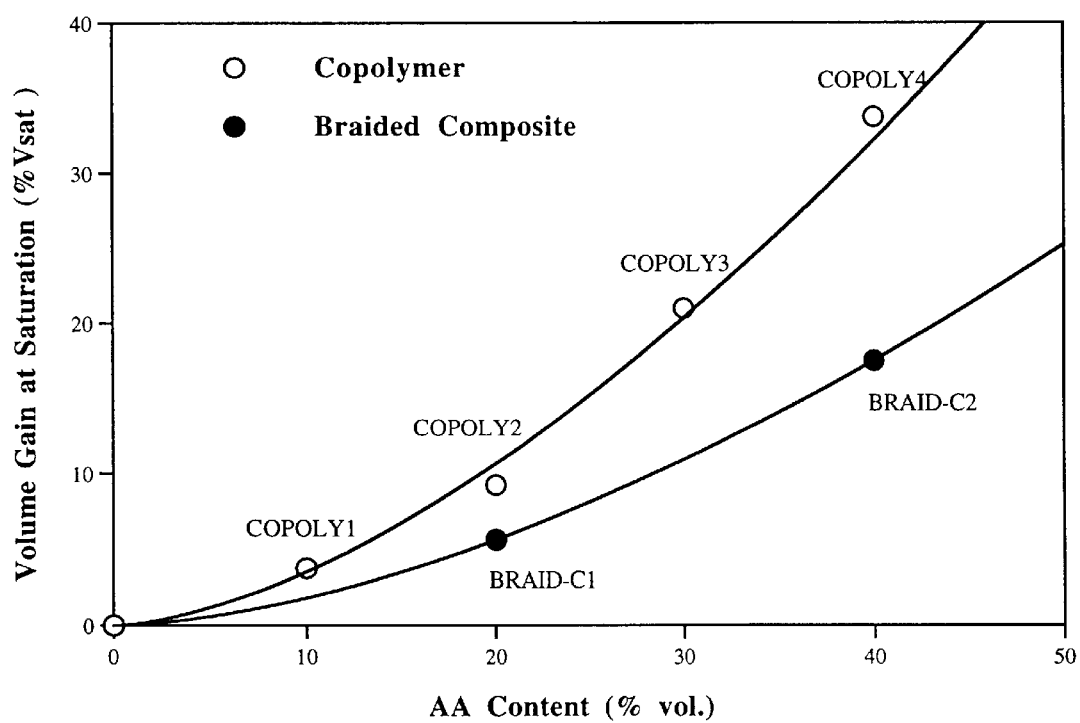
FIG. 14 is a graph depicting the effect of AA content on the saturated swelling levels of the copolymer and a circular braided composite.

In FIG. 14 there is shown the influence of the monomer ratio on the saturated swelling levels for both the copolymers (COPOLY# in Table 4) as well as the circular braided carbon reinforced composites (BRAID-C# in Table 4). Three samples were used for each set of measurements and the scatter within each set was minimal. These results clearly demonstrate that the swelling behavior of the copolymer or its composite can be effectively tailored by changing the relative amounts of MMA and AA in the matrix. The targeted free-swelling strain for the present application is about 1–2% (and may be about 3%) in the constrained implanted condition assuming that there is a perfect fit between the implant and bone (i.e., no clearance. This requirement corresponds roughly to about 5–10% in free-swelling when the typical levels of constraint imposed by the surrounding bone are accounted for and the fact that some clearance between the implant and bone is unavoidable from a practical viewpoint for the present application. From FIG. 14, it is clear that the ideal monomer ratio for the present application is about 80/20 (MMA/AA), since the saturated free swelling strain in this copolymer is about 9%, and for the carbon reinforced braided composite of this copolymer, it is about 5%.

Mechanical Properties

The studies performed below were conducted primarily under free-swelling conditions. It should be noted that the amount of swelling which occurs under constrained-swelling conditions is expected to be less than that which occurs under free-swelling conditions.

The another critical requirement (in addition to controlled swellability) for the present application is the ability of the material to retain its mechanical properties with swelling. Simple compression tests were performed on several sets of specimens of the copolymer and the composites produced in this study in both the dry and swollen states. The specimen ends were carefully machined and well lubricated using thin Teflon sheets and grease to prevent barreling and non-uniform deformation during testing. The tests were conducted at room temperature using a hydraulic MTS mechanical testing system (Model 312.21) using a cross-head speed of 1 mm/minute.

Figure 15:
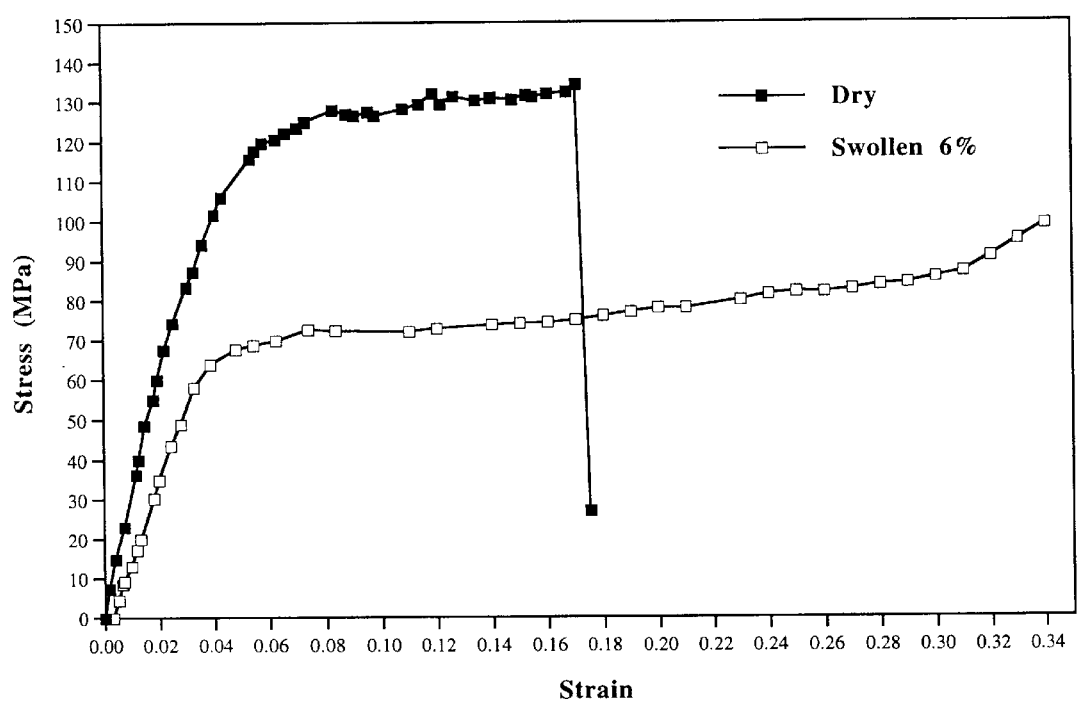
FIG. 15 is a graph depicting typical stress-strain curves of COPLY2 samples tested in dry and swollen (6%) conditions.

Typical stress-strain curves obtained for the 80/20 copolymer in dry and saturated conditions are shown in FIG. 15. It can be seen in this figure that the modulus (slope of the linear elastic part of the stress-strain curve) and the yield strength (value of stress where non-linearity initiates in this curve) decrease with swelling of the copolymer. However, the samples were able to sustain a larger amount of strain in the material before failure, usually shear failure or crushing of the sample. In other words, the area under the stress-strain curve increased with swelling indicating that the material can absorb more energy before failure. This is a clear indication that the material plasticizes or becomes rubbery with absorption of water, increasing its toughness while decreasing modulus and strength.

Figure 16:
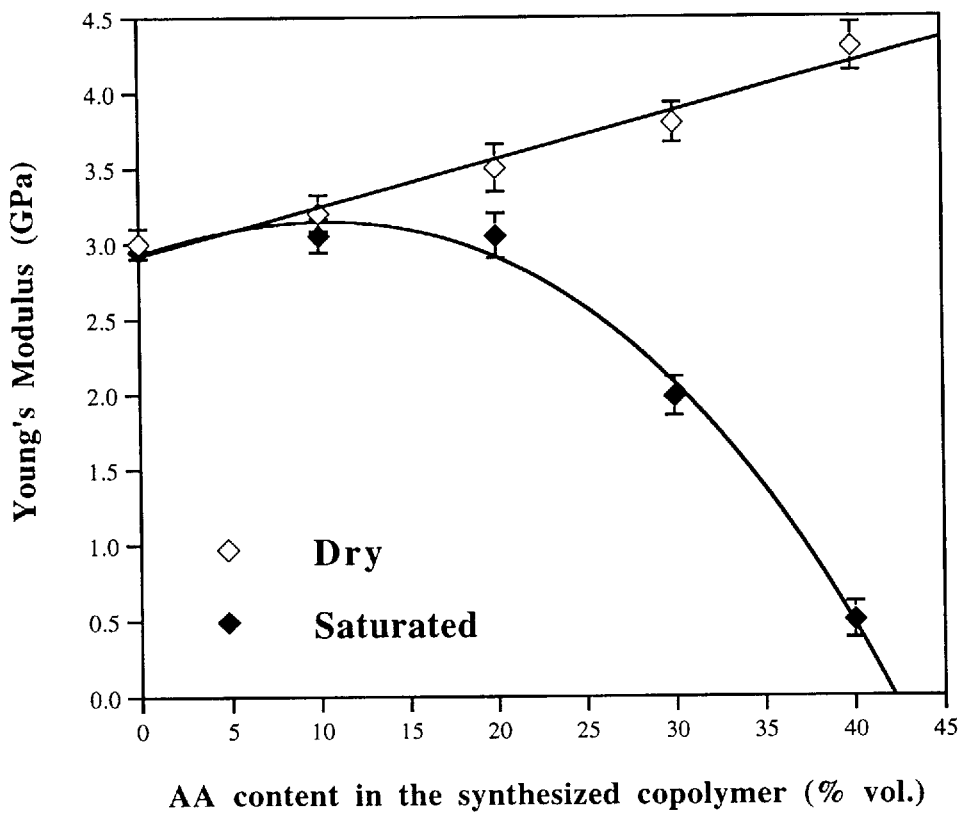
FIG. 16 is a graph depicting the variation of Young's moduli of dry and saturated copolymer samples with MMA/AA ratio.
Figure 17:
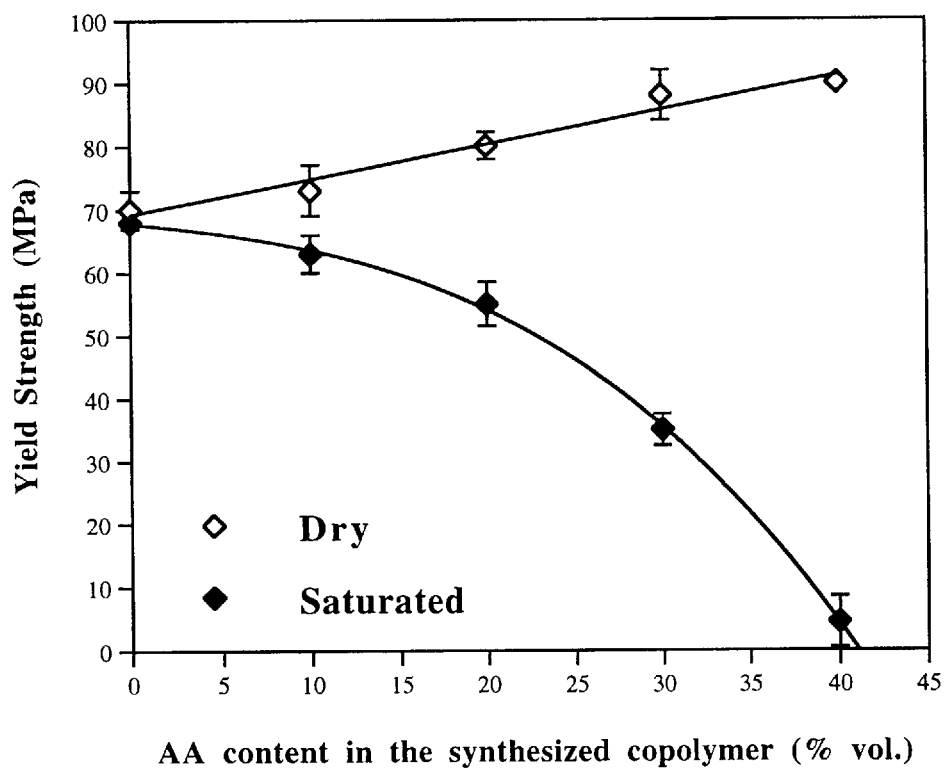
FIG. 17 is a graph depicting the variation in the yield strength of dry and saturated copolymer samples with MMA/AA ratio.
Figure 18:
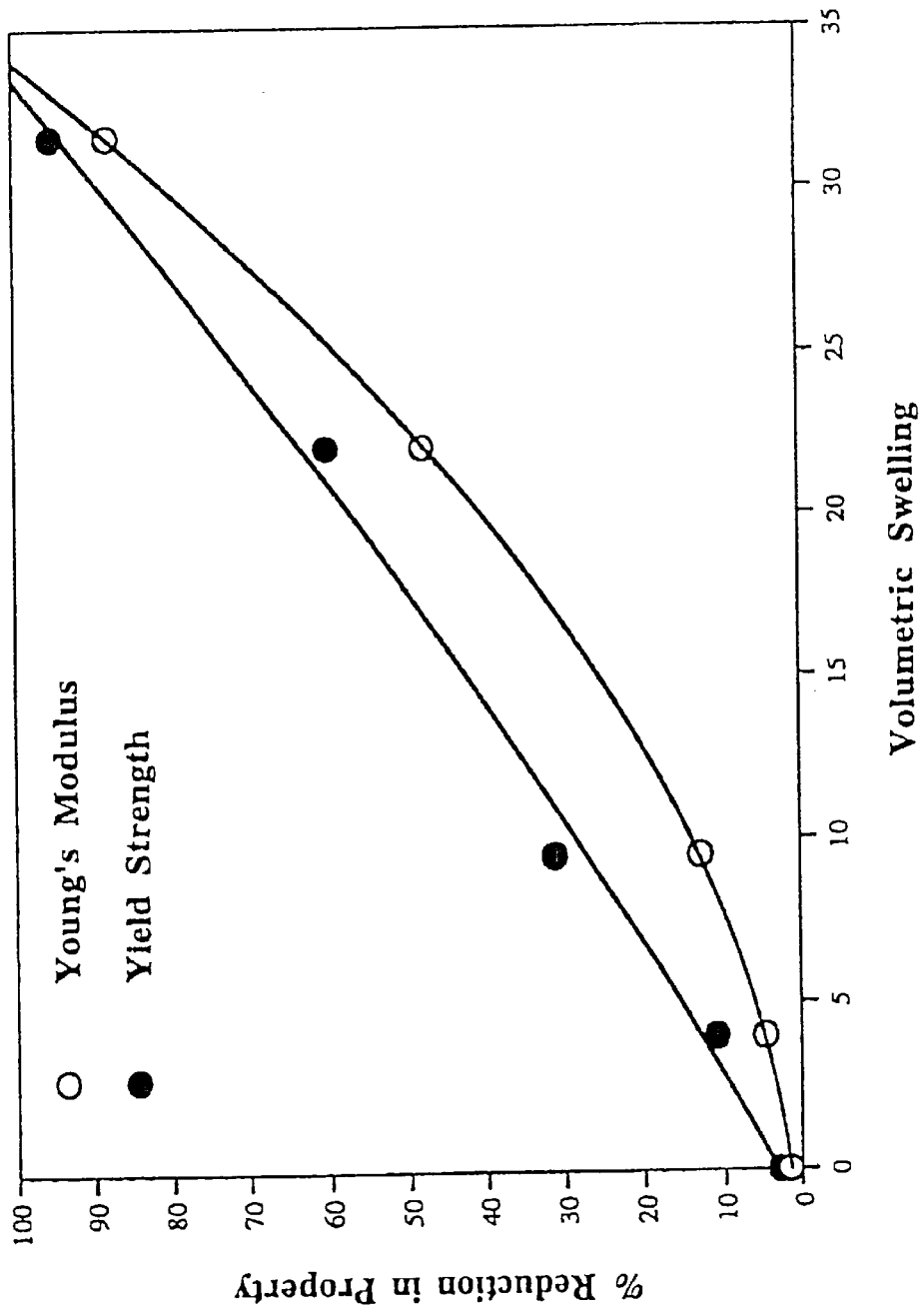
FIG. 18 is a graph depicting the percentage drop in Young'ss modulus and yield strength of the synthesized copolymer due to swelling.

In FIG. 16 there is shown the dependence of the Young's modulus of poly(MMA-AA) on its monomer content in both dry and saturated conditions. It can be seen that by increasing levels of AA content in the copolymer the dry modulus of the material increases. However, the modulus is decreased when the polymer is in the saturated condition. The corresponding data for the yield strength of the copolymer is shown in FIG. 17 and these data confirm the influence of the monomer content on the yield strength of the copolymer. The observed effects may be explained by the fact that an increase in the AA content in the copolymer results in an increase in the swellability of the copolymer (FIG. 14). The percentage loss in modulus and the percentage loss in the yield strength of the copolymer from the corresponding dry values are plotted in FIG. 18 as a function of the saturated swelling strain in the copolymer. These graphs demonstrate that the percentage drop in yield strength is typically larger than the percentage drop in modulus with swelling of the material, indicating that the yield strength is more sensitive to swelling of the material. The plot of percentage loss in modulus indicates that beyond a swelling strain of about 10%, degradation in modulus occurs at a faster rate (the curves becomes distinctly steeper beyond this swelling strain). It is clear that when swelling exceeds 10%, the copolymer plasticizes extensively and becomes very rubbery loosing practically all of its mechanical strength. These data therefore confirm that the ideal monomer ratio is about 80/20 (MMA/AA). It should be noted that the mechanical properties shown in FIGS. 16–18 correspond to saturated free swelling conditions, and that the loss of mechanical properties of the composite when in bone is expected to be lower because when the composite is in bone, the swelling is constrained.

Figure 19:
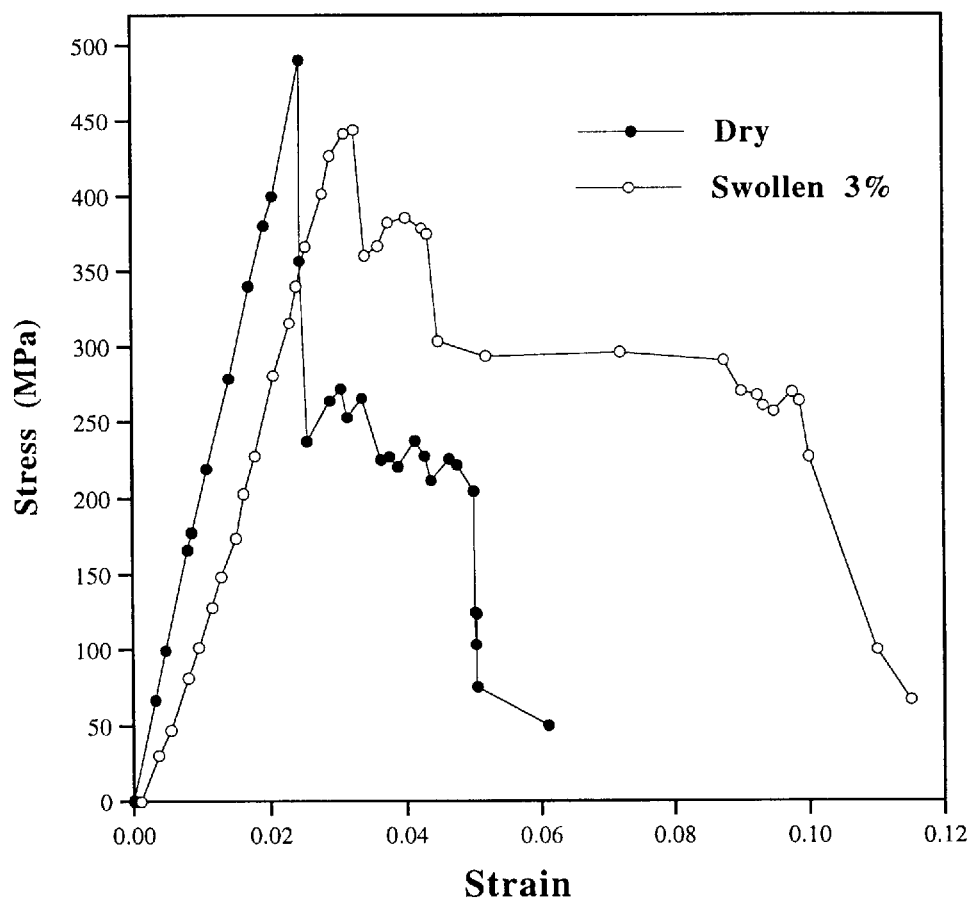
FIG. 19 is a graph depicting typical stress strain curves for UNIAX-C composite tested in dry and swollen conditions.

Typical stress-strain curves obtained for the unidirectional carbon reinforced composite (UNIAX-C in Table 4) in dry and swollen (3% by volume) conditions are shown in FIG. 19. Once again, a significant drop in modulus and yield strength of the composite with swelling is observed which is accompanied by a significant increase in the strain energy absorbed by the material prior to failure (area under the stress-strain curve). This increase in toughness of the material may be attributed to plasticization of the matrix due to absorption of water.

Three types of composite samples produced with the 80/20 copolymer matrix were tested in compression: UNIAX-C, UNIAX-K, and BRAID-C2 (see Table 4). The composite samples were tested in the longitudinal direction (along the fiber for unidirectional composites and along the braid axis for braided composites). The measured moduli and yield strengths for the various composites tested in this study are summarized in FIGS. 20 and 21, respectively. The values shown are the average values from about 4–5 measurements for each material system. For reference, the corresponding values for compact bone (cortical femur and titanium alloy (Ti-6Al-4V) are also included in these figures.

The values of the modulus and yield strength for Kevlar reinforced composites are relatively low compared with the other composites produced in this study. This is explained as follows: (i) The Kevlar fibers bend easily and therefore it is much more difficult (compared to carbon fibers) to keep them straight during processing. As a result, the fibers in Kevlar reinforced composite have more deviation from the axial direction compared with carbon fibers resulting in lower modulus and strength for the Kevlar reinforced composite. This is also confirmed by the degree of fiber buckling observed in the deformed samples of Kevlar reinforced composites compared to the carbon reinforced composites. (ii) Significant fiber/matrix debonding and fibrillation have been noted in Kevlar composites produced in this study.

Figure 20:
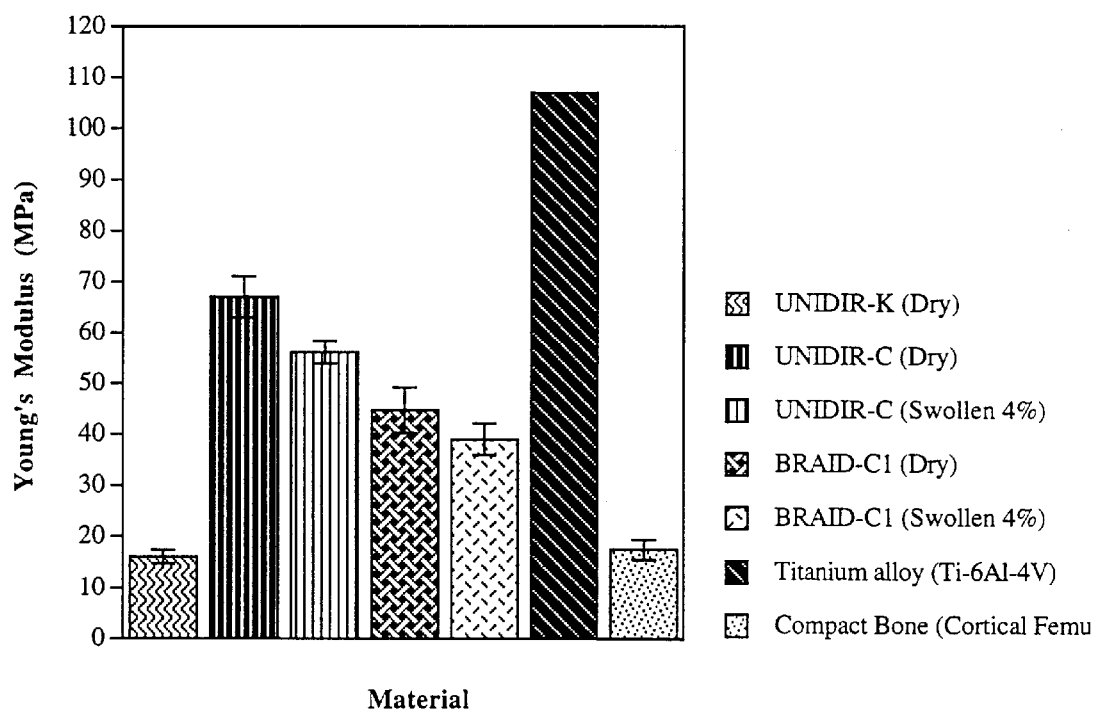
FIG. 20 is a graph depicting Young's moduli of different composites and a comparison of these moduli to those of cortical bone and Ti-6Al-4V Titanium alloy.
Figure 21:
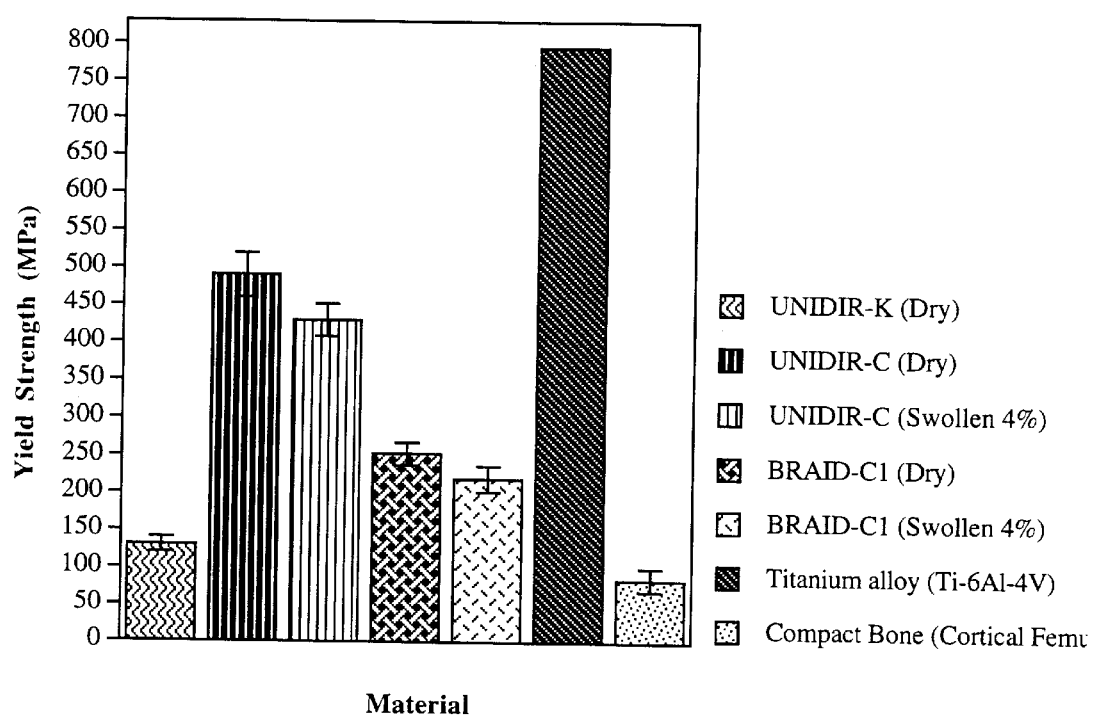
FIG. 21 is a graph depicting the yield strengths of different composites and a comparison of these yield strengths to those of cortical bone and Ti-6Al-4V Titanium alloy.

In FIG. 20 it can be seen that the modulus of the carbon reinforced composite produced in this study is much closer to the modulus of compact bone, when compared to the modulus of the titanium alloy. This fact provides yet another advantage for the novel bone implants of the present invention compared with traditional metallic bone implants since the differences in moduli of the bone and the implant are likely responsible for the stress shielding phenomenon which is believed to cause bone resorption and aseptic loosening. It should also be noted that the carbon reinforced composites tested in this study exhibited only a small loss in modulus (about 10–15%) with swelling and that the values of moduli are within the targeted range of 30–50GPa.

Push-Out Tests

Figure 22:
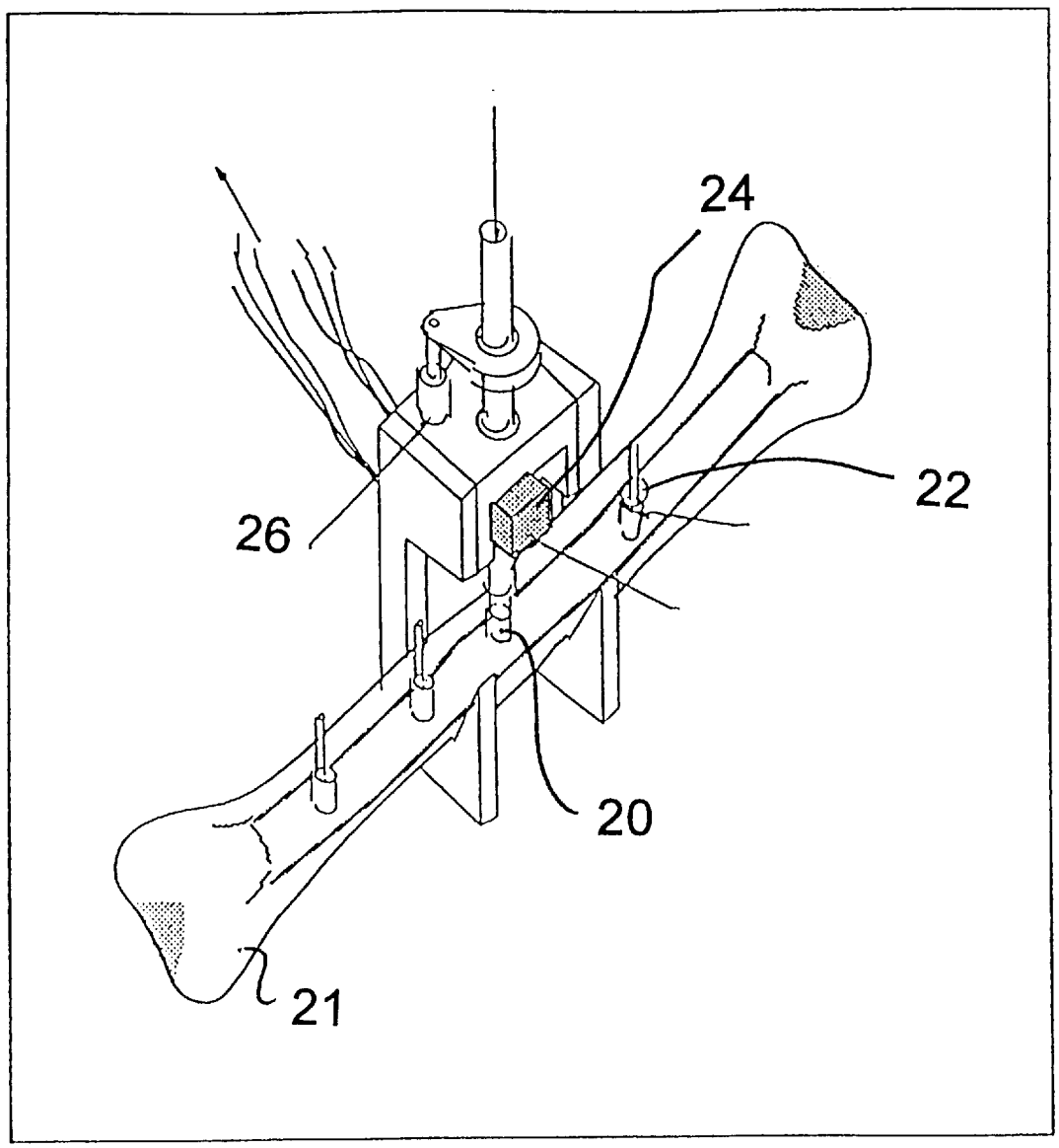
FIG. 22 is a schematic drawing of a push-out test.
Figure 23:
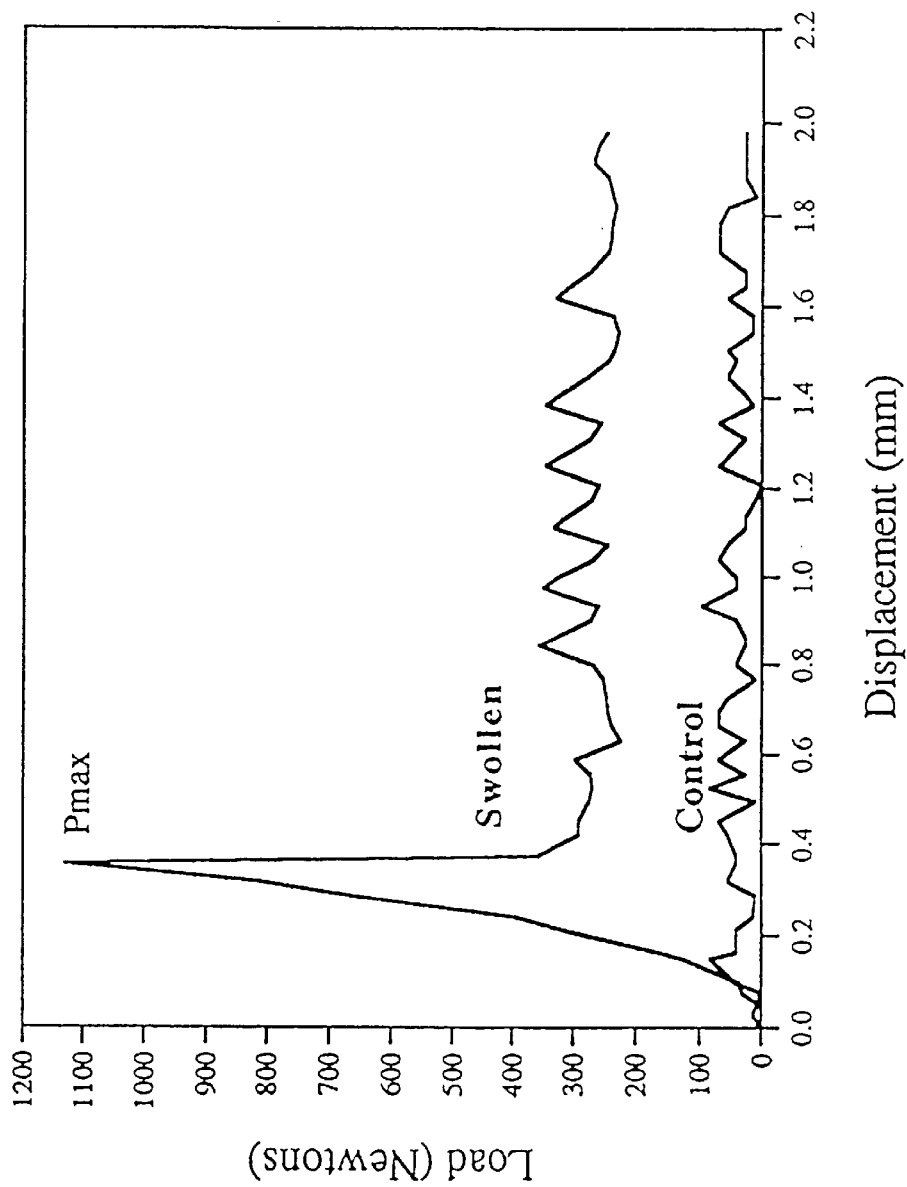
FIG. 23 is a graph depicting typical push-out load-displacement curves for composite samples implanted in bovine cortical bone for one week.

To characterize the fixation levels of the synthesized composite, a series of push-out tests on 80/20 (MMA/AA) matrix composite plugs 20 was conducted. The plugs 10 were 5 mm in diameter and 6 mm in height. They were implanted in bone by being press fit into drilled holes 22 in thick plates of bovine cortical bone 21. One half of the implanted samples were immersed in excess saline solution for one week and the other half remained untreated. A schematic drawing of the push-out test is shown in FIG. 22 and the typical push-out load-displacement curves are shown in FIG. 23. Force is measured by a load cell 24, and displacement is measured by a linear voltage differential transformer (LNDT) 26. The interfacial shear stress, calculated from the maximum recorded push-out loads (Pmax) divided by the surface contact area of the plugs and bone, were used to characterize fixation levels. The values which were obtained for interfacial shear stress of the swollen samples were in the range of 7.0–9.0 MPa accompanied by only 2–3% gain in weight. In contrast, values for the control, untreated samples were less than 0.5 MPa. These results clearly demonstrate the fixation mechanism, i.e., the expansion-fit mechanism of the composites of the present invention in bone.

Figure 24:
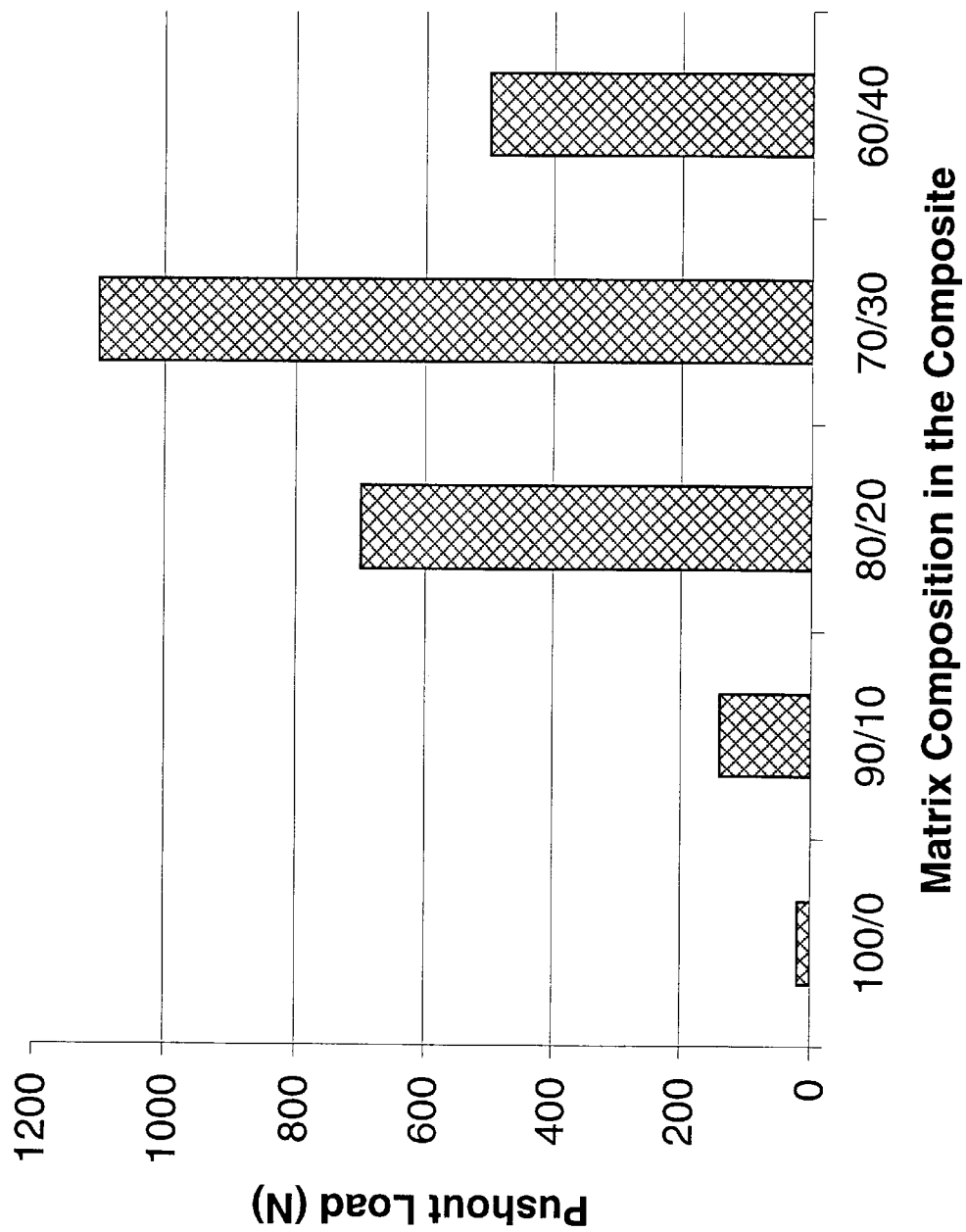
FIG. 24 is a graph depicting the push-out loads of composite plugs having various matrix compositions.
Figure 25:
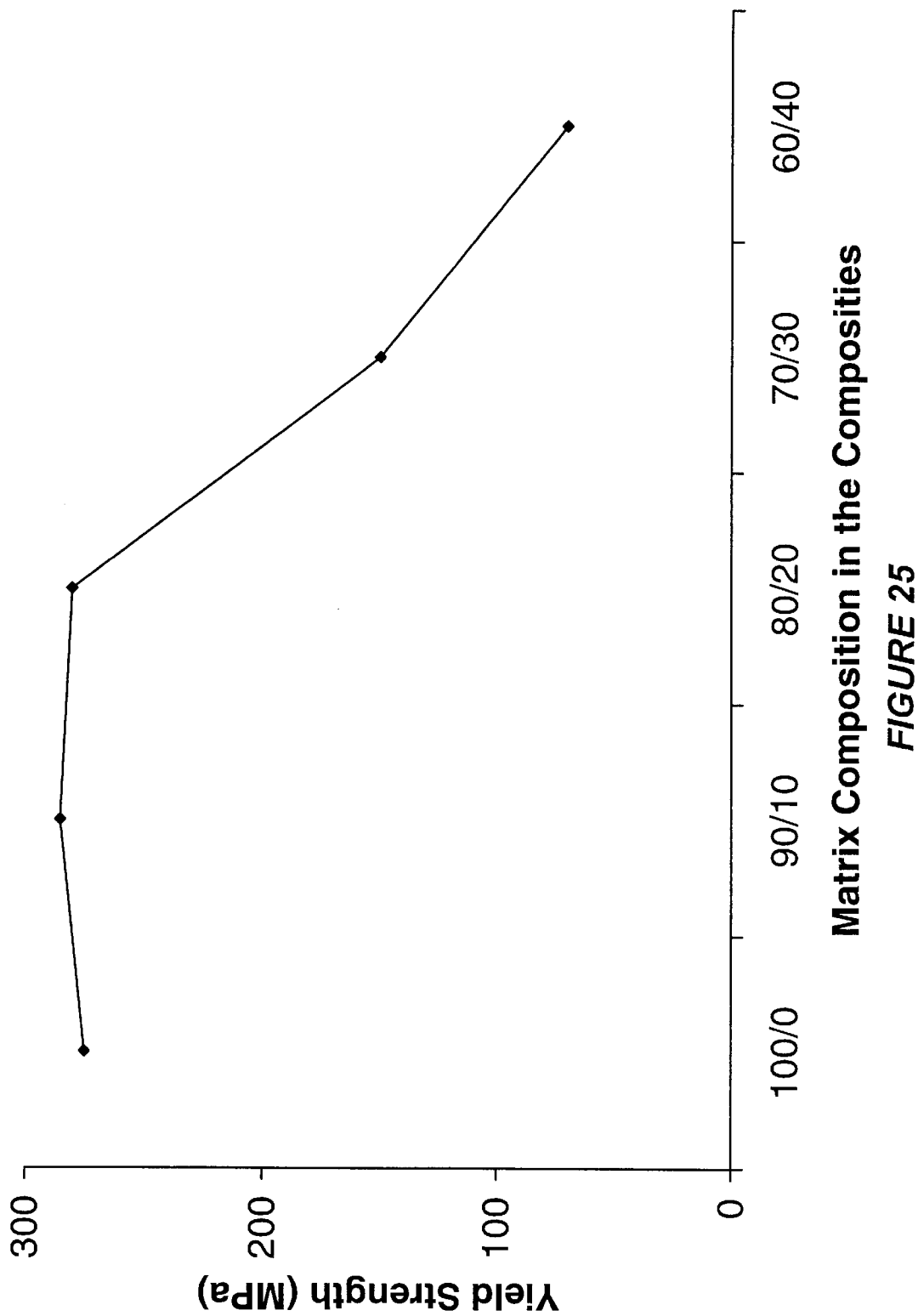
FIG. 25 is a graph depicting compressive yield strengths of composite plugs tested following implantation into bone.

When the ratio of MMA/AA was varied in the composite, the results shown in FIG. 24 were obtained. These results indicate that the fixation levels of the implant increase with the hydrophilic ratio in the matrix and reach a maximum value in samples containing 30% AA, i.e., those samples having 70/30 MMA/AA. Additional increase in the relative amount of the hydrophilic component did not result in any improvement in the fixation levels. Further, as shown in FIG. 25, the compressive yield strength of the pushed-out composite plugs were maximal at a MMA/AA composition of 80/20 and were distinctly lower at a MMA/AA composition of 70/30.

A temporal study was conducted to evaluate the dependence of the holding power and shear strength on the time of implantation of the composite into the bone. This information provides estimates on the length of time that the patient may need to be bedridden following implantation of the composite. To perform this study, 80/20 MMA/AA-graphite samples were implanted into bovine cortical bone for 1, 2, 5, 7, 14 and 28 days. Push-out tests were conducted at each time period and shear stress was measured. Approximately 50% of the holding power of the samples was achieved by 7 days following implantation. After 7 days, any increase in the shear resistance was relatively low. However, a relatively wide range for the push-out strength was observed at each time period.

In summary, a matrix composition ranging from 80/20 to 70/30 MMA/AA results in high fixation levels without significant loss in mechanical properties when implanted into bone. The preferred ratio of MMA/AA in the composite is 80/20.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of anchoring soft tissue to bone comprising:
   providing a mixture of a hydrophobic monomer and a hydrophilic monomer and a crosslinking agent to form a swellable copolymer;
   adding a soft tissue attachment element to said mixture, wherein a portion of said soft tissue attachment element protrudes from said mixture;
   polymerizing said mixture to form said copolymer;
   implanting said copolymer into bone and attaching a soft tissue to said protruding portion of said attachment element to anchor said soft tissue to said bone.

2. The method or claim 1, wherein said hydrophobic monomer is methyl methacrylate.

3. The method of claim 2, wherein said hydrophilic monomer is acrylic acid.

4. The method of claim 3, wherein the ratio of methyl methacrylate to acrylic acid is from about 60/40 to about 90/10.

5. The method of claim 4, wherein said ratio is from about 70/30 to about 80/20.

6. The method of claim 5, wherein said ratio is 80/20.

7. The method of claim 3, wherein said crosslinking agent is selected from the group consisting of allyl methacrylate and diethylene glycol dimethacrylate.

8. The method of claim 7, wherein said crosslinking agent is allyl methacrylate.

9. The method of claim 3, wherein said mixture further comprises biocompatible fibers.

10. The method of claim 9, wherein said biocompatible fibers are selected from the group consisting of carbon fibers and Kevlar fibers.

11. The method of claim 10, wherein said fibers are carbon fibers.

12. The method of claim 9, wherein said biocompatible fibers are oriented in said copolymer in one direction.

13. The method of claim 9, wherein said biocompatible fibers are in a braided orientation.

14. The method of claim 9, wherein said biocompatible fibers are chopped fibers.

15. The method of claim 3, wherein said soft tissue attachment element is inserted into said mixture prior to polymerization of said copolymer.

16. The method of claim 3, wherein said soft tissue attachment element is wound around said copolymer after polymerization of said copolymer.

17. The method of claim 3, wherein said soft tissue attachment element is a metal.

18. The method of claim 3, wherein said soft tissue attachment element is flexible material.

19. The method of claim 18, wherein said soft tissue attachment element is a suture-like material.

20. The method of claim 18, wherein said soft tissue attachment element is a suture.

21. A composite for anchoring soft tissue to bone comprising methyl methacrylate and acrylic acid in a ratio of 80/20, allyl methacrylate, braided carbon fibers, in combination with a soft tissue attachment element attached to said composite material so as to partially project therefrom.

22. A preformed object for anchoring soft tissue to bone comprising a composite material comprising a copolymer comprising methyl methacrylate and acrylic acid in a ratio of 80/20 and allyl methacrylate, and a soft tissue attachment element attached to said composite material so as to partially project therefrom.

23. The preformed object of claim 22, wherein said composite comprises biocompatible fibers.

24. The preformed object of claim 22, wherein said composite material is shaped in a form selected from the group consisting of a screw, a pin and a staple.

25. The preformed object of claim 22, wherein said soft tissue attachment element is selected from the group consisting of a screw, a pin and a suture.

* * * * *